United States Patent
Baker et al.

(10) Patent No.: US 9,872,849 B2
(45) Date of Patent: Jan. 23, 2018

(54) DITERPENOID MEMBRANOLIDE COMPOUNDS HAVING ANTI-LEISHMANIA ACTIVITY AND USES THEREOF

(71) Applicants: Bill J. Baker, Tampa, FL (US); Christopher G. Witowski, Clearwater, FL (US); John Alan Maschek, Salt Lake City, UT (US); Brian Vesely, Tampa, FL (US); Dennis E. Kyle, Lithia, FL (US)

(72) Inventors: Bill J. Baker, Tampa, FL (US); Christopher G. Witowski, Clearwater, FL (US); John Alan Maschek, Salt Lake City, UT (US); Brian Vesely, Tampa, FL (US); Dennis E. Kyle, Lithia, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 72 days.

(21) Appl. No.: 14/811,341

(22) Filed: Jul. 28, 2015

(65) Prior Publication Data
US 2016/0030388 A1    Feb. 4, 2016

Related U.S. Application Data

(60) Provisional application No. 62/032,243, filed on Aug. 1, 2014.

(51) Int. Cl.
| | |
|---|---|
| *A61K 31/365* | (2006.01) |
| *A61K 45/06* | (2006.01) |
| *A61K 31/343* | (2006.01) |
| *A61K 31/366* | (2006.01) |

(52) U.S. Cl.
CPC .......... *A61K 31/365* (2013.01); *A61K 31/343* (2013.01); *A61K 31/366* (2013.01); *A61K 45/06* (2013.01)

(58) Field of Classification Search
CPC .... A61K 31/365; A61K 31/366; A61K 45/06; A61K 31/343
USPC .............. 514/31, 311, 35, 455, 456, 470, 77
See application file for complete search history.

(56) References Cited

PUBLICATIONS

Sundar et al. Single-Dose Liposomal Amphotericin B for Visceral Leishmaniasis in India. N Engl J Med 362:504-512, 2010.*
Gupta et al. Prediction of Medicinal Properties of Marine Biota using Computational Bioinformatics Techniques. Asian Journal of Biological Sciences 4 (8): 575-590, 2011.*
Ankisetty, S., et al., "Further Membranolide Diterpenes from the Antarctic Sponge *Dendrilla membranosa*," *Journal of Natural Products*, 2004, vol. 67, pp. 1172-1174.
Baker, B.J., et al., "Chemical and Ecological Studies of the Antarctic Sponge *Dendrilla membranosa*," *Journal of Natural Products*, 1995, vol. 58, pp. 1459-1462.
Bero, J., et al., "In vitro antitrypanosomal and antileishmanial activity of plants used in Benin in traditional medicine and bio-guided fractionation of the most active extract," *Journal of Ethnopharmacology*, 2011, vol. 137, No. 2, pp. 998-1002.
Bilbao-Ramos, P., et al., "A fluorometric method for evaluation of pharmacological activity against intracellular *Leishmania* amastigotes," *Journal of Microbiological Methods*, 2012, vol. 89, pp. 8-11.
Boelaert, M., et al., "A Comparative Study of the Effectiveness of Diagnostic Tests for Visceral Leishmaniasis," *American Journal of Tropical Medicine and Hygiene*, 2004, vol. 70, pp. 72-77.
Croft, S.L., et al., "Drug Resistance in Leishmaniasis," *Clinical Microbiology Reviews*, 2006, vol. 19, No. 1, pp. 111-126.
Fontana, A., et al., "Dendrinolide, a New Degraded Diterpenoid frm the Antarctic Sponge *Dendrilla membranosa*," *Journal of Natural Products*, 1997, vol. 60, pp. 475-477.
Goswami, R.P., et al., "K39 Strip Test—Easy, Reliable and Cost-Effective Field Diagnosis for Visceral Leishmaniasis in India," *Journal of the Association of Physicians of India*, 2003, vol. 51, pp. 759-761.
Guerin, P.J., et al., "Visceral leishmaniasis: current status of control, diagnosis, and treatment, and a proposed research and development agenda," *Lancet Infectious Diseases*, 2002, vol. 2, pp. 494-501.
Hanson, W.L., et al., "Testing of Drugs for Antileishmanial Activity in Golden Hamsters Infected with *Leishmania donovani*," *International Journal for Parasitology*, 1977, vol. 7, No. 6, pp. 443-447.
Manriquez, V., et al., "Structure of membranolide, a diterpene from the Antarctic Sponge *Dendrilla membranosa*," *Acta Crystallographica Section C*, 1990, vol. 46, pp. 2486-2487.
Maschek, J.A., "Chemical Investigation of the Antarctic Marine Invertebrates Austrodoris kerguelensis & Dendrilla membranosa and the Antarctic Red Alga Gigartina skottsbergii," Ph.D. Dissertation, University of South Florida, Jun. 7, 2011.
Molinski, T.F., et al., "Metabolites of the Antarctic Sponge *Dendrilla membranosa*," *Journal of Organic Chemistry*, 1997, vol. 62, pp. 960-966.
Murray, H.W., "Treatment of Visceral Leishmaniasis in 2004," *American Journal of Tropical Medicine and Hygiene*, 2004, vol. 71, No. 6, pp. 787-794.
Singh, S., et al., "New developments in diagnosis of leishmaniasis," *Indian Journal of Medical Research*, 2006, vol. 123, pp. 311-330.
Sobarzo-Sánchez, E., et al., "Synthetic Oxoisoaporphine Alkaloids: In Vitro, In Vivo and In Silico Assessment of Antileishmanial Activities," *PLOS ONE*, 2013, vol. 8, No. 10, Article No. e77560.
Puliti, R., et al., "Structure of a keto derivative of 9,11-dihydrogracilin A," *Acta Crystallographica Section C*, 1993, vol. 49, pp. 1373-1376.

(Continued)

*Primary Examiner* — Yih-Horng Shiao
(74) *Attorney, Agent, or Firm* — Saliwanchik Lloyd & Eisenschenk

(57) ABSTRACT

In a screening program, the Antarctic sponge *Dendrilla membranosa* was found to produce diterpenoid secondary metabolites with activity against the leishmaniasis-causing parasite *Leishmania donovani*. The present invention concerns compositions useful for control of *Leishmania* spp. parasites in vitro and in vivo and treatment of leishmaniasis; methods for treatment of leishmaniasis; and methods for controlling *Leishmania* spp. parasites in vitro and in vivo.

8 Claims, 4 Drawing Sheets

(56) References Cited

PUBLICATIONS

Riera, C., et al., "Evaluation of a latex agglutination test (KAtex) for detection of *Leishmania* antigen in urine of patients with HIV-*Leishmania* coinfection: value of diagnosis and post-treatment follow-up," *European Journal of Clinical Microbiology & Infectious Diseases*, 2004, vol. 23, No. 12, pp. 899-904.

Rijal, S., et al., "Evaluation of a urinary antigen-based latex agglutination test in the diagnosis of kala-azar in eastern Nepal," *Tropical Medicine and International Health*, 2004, vol. 9, pp. 724-729.

Rocha, M.N., et al., "Cytotoxicity and In Vitro Antileishmanial Activity of Antimony (V), Bismuth (V), and Tin (IV) Complexes of Lapachol," *Bioinorganic Chemistry and Applications*, 2013, vol. 2013, pp. 1-7.

Tariku, Y., et al., "In Vitro Evaluation of Antileishmanial Activity and Toxicity of Essential Oils of *Artemisia absinthium* and *Echinops kebericho*," *Chemistry & Biodiversity*, 2011, vol. 8, No. 4, pp. 614-623.

Tasdemir, D., et al., "Antitrypanosomal and Antileishmanial Activities of Flavonoids and Their Analogues: In Vitro, In Vivo, Structure-Activity Relationship, and Quantitative Structure-Activity Relationship Studies," *Antimicrobial Agents and Chemotherapy*, 2006, vol. 50, No. 4, pp. 1352-1364.

Vanloubbeeck, Y., et al., "The Immunology of *Leishmania* Infection and the Implications for Vaccine Development," *Annals of the New York Academy of Sciences*, 2004, vol. 1026, pp. 267-272.

Witowski, C. et al. "Characterization of membranolides B-H from Dendrilla membranosa and their activity against leishmaniasis" *Planta Medica*, 2014, 80—PB8, abstract.

Witowski, C. et al. "Characterization of Membranolides B-H from *Dendrilla membranosa* and Their Activity Against Leishmaniasis" poster presented at Annual Meeting of the American Society of Pharmacognosy, Oxford, MS, Aug. 2014.

\* cited by examiner

DITERPENOID MEMBRANOLIDE COMPOUNDS HAVING ANTI-LEISHMANIA ACTIVITY AND USES THEREOF

CROSS-REFERENCE TO RELATED APPLICATION

The present application claims the benefit of U.S. Provisional Application Ser. No. 62/032,243, filed Aug. 1, 2014, which is hereby incorporated by reference herein in its entirety, including any figures, tables, nucleic acid sequences, amino acid sequences, or drawings.

GOVERNMENT SUPPORT

This invention was made with government support under grant number ANT0828776 awarded by the National Science Foundation and grant number R21 AI103673 awarded by the National Institutes of Health. The government has certain rights in the invention.

BACKGROUND OF THE INVENTION

Leishmaniasis is a parasitic disease that is found in parts of the tropics, subtropics, and southern Europe. It is classified as a neglected tropical disease (NTD), affects nearly one million people per year, and can be fatal if left untreated. Leishmaniasis is caused by infection with *Leishmania* parasites, which are spread by the bite of infected sand flies. There are several different forms of leishmaniasis in people. The most common forms are cutaneous leishmaniasis, which causes skin sores, and visceral leishmaniasis, which affects several internal organs. Known treatments for leishmaniasis include amphotericin B, a combination of antimonials and paramomycin, and miltefosine, with each having its own efficacy, advantages, and disadvantages.

In the field of natural products, compounds from the terrestrial realm have represented much of the literature due to the accessibility of plants and their use in traditional medicine. It was not until the 1950s that the concept of "drugs from the sea" would begin to gain momentum, at least partly due to advancement in collection techniques, i.e., SCUBA diving. Marine sponges have proven a rich source of secondary metabolites among the Antarctic invertebrates. Many of these secondary metabolites are bioactive, with some causing feeding deterrence in ecologically relevant predators and some displaying potent antimicrobial or cytotoxicity properties. The bright yellow Antarctic cactus sponge, *Dendrilla membranosa* Pallas (family Darwinellidae, order Dendroceratida) is a dominant demosponge that prior studies have shown is rarely preyed upon and deters feeding against amphipods, the principal mesograzers of the Western Antarctic Peninsula (WAP). Along the WAP, macroalgal forests dominate the shallow benthos and colorful invertebrates cover stunning walls that drop straight to the ocean floor. The chemical ecology of the current benthic marine invertebrate fauna is largely ancient and endemic. The diversity rivals that of temperate and tropical climates, though key differences in ecology dictated by physical pressures such as the Antarctic Circumpolar Current (ACC) and repeated periods of glaciations have sculpted a unique environment.

Diterpenes have been isolated from sponges of the orders of Dendroceratida and Dictyocertida. *D. Membranosa* collected from McMurdo Sound, Antarctica, has been shown to yield highly oxidized diterpenes, including gracilin derivatives, and the aromatized diterpene membranolide A (Molinski T F et al., *J. Org. Chem.*, 1987, 52:296-298; Manriquez V et al., *Acta Crystallogr. Sect. C*, 1990, 46:2486-2487; Puliti R et al., *Acta Crystallogr. Sect. C*, 1993, 49:1373-1376; Baker B J et al., *J Nat. Prod.*, 1995, 58:1459-1462; and Fontana A et al., *J. Nat. Prod.*, 1997, 60:475-477). The isolation of membranolide-type diterpenes from *D. membranosa* collected from Palmer Station on Anvers Island, Antarctica, has been reported (Ankisetty S et al., *J. Nat. Prod.*, 2004, 67:1172-1174).

BRIEF SUMMARY OF THE INVENTION

Leishmaniasis is a neglected tropical disease that affects nearly one million people per year and can be fatal if left untreated. In a screening program, the Antarctic sponge *Dendrilla membranosa* was found to produce diterpenoid secondary metabolites with activity against the leishmaniasis-causing parasite *Leishmania donovani*. Dichloromethane/methanol (1:1) extracts of the sponge yielded aplysulphurin, its tetrahydro-derivative, and a suite of membranolides, some of which displayed potent bioactivity. In an investigation of membranolides B—H, aplysulphurin was subjected to methanolic treatments and the newly formed compounds were isolated. Upon characterization, these compounds showed identical spectral characteristics to the methoxy-bearing membranolides. The $IC_{50}$ values of these compounds were assessed in a structure activity relationship (SAR) study targeting anti-leishmanial efficacy.

Aplysulphurin (compound 1) is a diterpene in sponges such as the Antarctic sponge *Dendrilla membranosa*. Crude dichloromethane/methanol (1:1) extracts from this sponge were determined by the inventors to exhibit activity against the parasite that causes visceral leishmaniasis, *Leishmania donovani*. Chromatographic separation of the *D. membranosa* extract lead to the isolation of aplysulphurin and tetrahydroaplysulphurin (compound 2) as the predominant antileishmanial products. Further studies of aplysulphurin found that treatment with methanol produced a series of semisynthetic derivatives based on the membranolide A (compound 3) skeleton, including aldehyde-bearing derivatives (membranolides B and E; compounds 4 and 5, respectively), diacetal derivatives (membranolides C, D, G, and H; compounds 6-9, respectively), and an oxidation product, lactone (membranolide F; compound 10).

One aspect of the invention is a composition comprising an isolated compound having the structure of formula (I), or a pharmaceutically acceptable salt thereof; and an anti-*Leishmania* agent. In some embodiments, the compound has the structure of formula (II), (III), or (IV), or a pharmaceutically acceptable salt thereof. In some embodiments, the compound is aplysulphurin (compound 1), tetrahydroaplysuphurin (compound 2), membranolide A (compound 3), membranolide B (compound 4), membranolide C (compound 6), membranolide D (compound 7), membranolide E (compound 5), membranolide F (compound 10), or membranolide G (compound 8), or membranolide (H) (compound 9), having a structure shown in FIG. 1, or a pharmaceutically acceptable salt thereof. In other embodiments, the compound is not a compound having a structure shown in FIG. 1 or a pharmaceutically acceptable salt thereof. The composition may further include a pharmaceutically acceptable carrier. In some embodiments, the anti-*Leishmania* agent is an antimonial (e.g., pentavalent antimonials such as sodium stibogluconate, meglumine antimonite), amphotericin B (e.g., conventional or liposomal), miltefosine (hexadecylphosphocholine), pentamidine, aminoglycoside-amino-cyclitol antibiotic (e.g., paromycin), azole (e.g., ketoconazole, itraconazole, fluconazole), 4-methyl-6-methoxy-8-aminoquinoline (e.g., sitamaquine), or nucleoside analogue (such as a pyrazolopyrimidine, e.g., allopurinol), or a combination of two or more of the foregoing.

Another aspect of the invention is a method for treatment of leishmaniasis, comprising administering an effective amount of a compound having the structure of formula (I), or a pharmaceutically acceptable salt thereof, to a subject. In some embodiments, the compound has the structure of formula (II), (III), or (IV), or a pharmaceutically acceptable salt thereof. In some embodiments, the compound is aplysulphurin (compound 1), tetrahydroaplysuphurin (compound 2), membranolide A (compound 3), membranolide B (compound 4), membranolide C (compound 6), membranolide D (compound 7), membranolide E (compound 5), membranolide F (compound 10), or membranolide G (compound 8), or membranolide (H) (compound 9), having a structure shown in FIG. 1, or a pharmaceutically acceptable salt thereof. In other embodiments, the compound is not a compound having a structure shown in FIG. 1 or a pharmaceutically acceptable salt thereof.

Optionally, other biologically active agents, such as one or more additional membranolide compounds of formula (I) or other anti-*Leischmania* agents, may be administered to the subject, either within the same composition as the membranolide(s) of formula (I) or in one or more separate compositions.

Another aspect of the invention concerns a method for controlling *Leishmania* spp. parasites, comprising applying an effective amount of a compound having the structure of formula (I), or a pharmaceutically acceptable salt thereof, to a *Leishmania* parasite, or to the situs of a *Leishmania* parasite, in vitro or in vivo. In some embodiments, the *Leishmania* parasite is *L. aethiopica, L. amazonensis, L. arabica, L. braziliensis, L. dovani (L. dovani dovani, L. dovani infantum, L. dovani chagasi), L. enrietti, L. gerbilli, L. hertigi, L. infantum, L. killicki, L. major, L. martiniquensis, L. mexicana (L. mexicana mexicana, L. mexicana amazonensis, L. mexicana pifanoi), L. peruviana, L. siamensis, L. tropica,* or *L. turanica*. In some embodiments, the compound has the structure of formula (II), (III), or (IV), or a pharmaceutically acceptable salt thereof. In some embodiments, the compound is aplysulphurin (compound 1), tetrahydroaplysuphurin (compound 2), membranolide A (compound 3), membranolide B (compound 4), membranolide C (compound 6), membranolide D (compound 7), membranolide E (compound 5), membranolide F (compound 10), or membranolide G (compound 8), or membranolide (H) (compound 9), having a structure shown in FIG. 1, or a pharmaceutically acceptable salt thereof. In other embodiments, the compound is not a compound having a structure shown in FIG. 1 or a pharmaceutically acceptable salt thereof.

Optionally, other biologically active agents, such as one or more additional membranolide compounds of formula (I) or other anti-*Leischmania* agents, may be applied to the *Leishmania* parasite, or to the situs of a *Leishmania* parasite, in vitro or in vivo, either within the same composition as the membranolide(s) of formula (I) or in one or more separate compositions.

DETAILED DESCRIPTION OF THE INVENTION

The inventors have investigated the trophic interactions of Antarctic invertebrates for some time. Previous studies have examined sponge-amphipod interactions by developing a bioassay to examine the feeding deterrent properties of sponge extracts and compounds. Of 12 species of common demosponges, only two exhibited significant feeding deterrence against the amphipod *Gondogeneia antarctica*: both the lipophilic and hydrophilic extracts from *Crella* sp. and the lipophilic extract from *Dendrilla membranosa* (P=0.022).

The slow-growing, yellow sponge *D. membranosa* is abundant in shallow waters (up to 40 m) on the Western Antarctic Peninsula benthos. Previous extractions yielded a suite of oxidized diterpenes with varying degrees of biological activity. The presence of methoxy groups in the membranolides sparked a re-investigation of these compounds formed from methanolic solvent treatments.

In a screening program, the Antarctic sponge *Dendrilla membranosa* was found to produce diterpenoid secondary metabolites with activity against the leishmaniasis-causing parasite *Leishmania donovani*. Dichloromethane/methanol (1:1) extracts of the sponge yielded aplysulphurin, its tetrahydro-derivative. In an investigation of membranolides B—H, aplysulphurin was subjected to methanolic treatments and the newly formed compounds were isolated. The bioactivity of these compounds toward *L. donovani* found two semisynthetic derivatives as potent and selective inhibitors.

Figure 1:
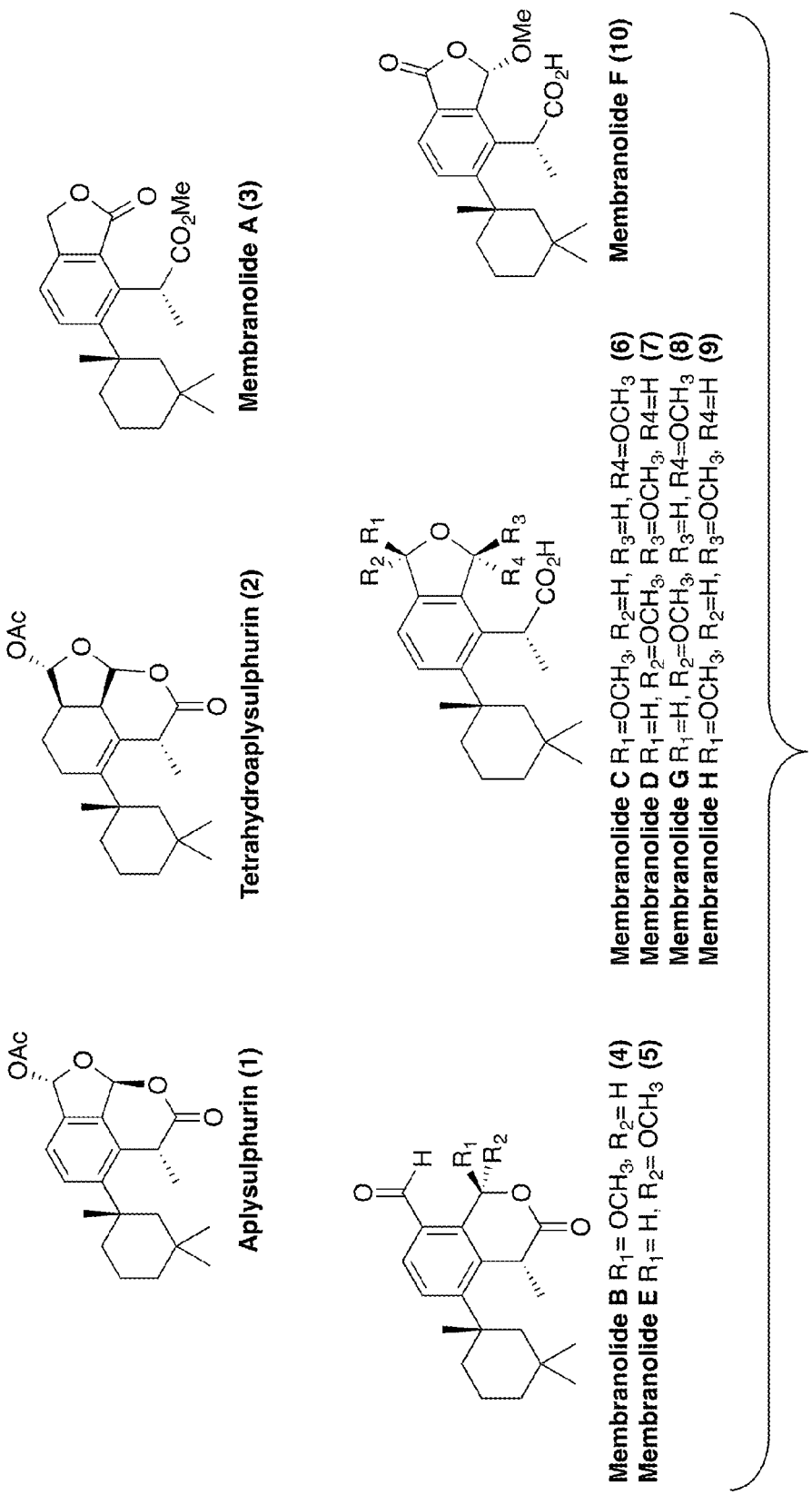
FIG. 1 shows the chemical structures of diterpenoid membranolides obtained from *D. membranosa*, including aplysulphurin (compound 1), tetrahydroaplysulphurin (compound 2), membranolide A (compound 3), membranolide B (compound 4), membranolide E (compound 5), membranolide C (compound 6), membranolide D (compound 7), membranolide G (compound 8), membranolide H (compound 9), and membranolide F (compound 10).

From the lipophilic extract of *D. membranosa*, eight fractions were generated via normal-phase (NP) medium-pressure liquid chromatography (MPLC), four of which exhibited anti-feeding activity. The spectroscopic data from these active fractions showed characteristic signals of the membranolides, a series of diterpenoids previously implicated in the chemical defense of *D. membranosa*. The structures of the isolated compounds are shown in FIG. 1.

The isolation and characterization of membranolide-type diterpenes from *D. membranosa* has been described (Ankisetty S et al., *J. Nat. Prod.,* 2004, 67:1172-1174; and Maschek, J. A. Dissertation, "Chemical Investigation of the Antarctic Marine Invertebrates *Austrodoris kerguelenensis* & *Dendrilla membranosa* and the Antarctic Red Alga *Gigartina skottsbergii*", University of South Florida. 2011, Chapter 4, pages 113-142, each of which is incorporated herein by reference in its entirety).

An aspect of the invention is a composition which may be used for treatment of leishmaniasis and for controlling *Leishmania* spp. parasites in vitro or in vivo, wherein the composition comprises an anti-*Leishmania* agent; and a compound having the following structure:

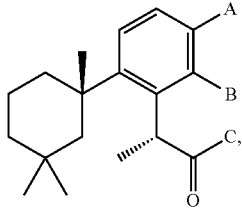

(I)

wherein A-B—C is:

or
when A-B is:

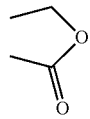

and C is:

 —OMe, or
when A-B is

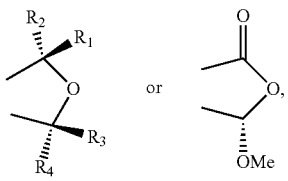

and C is:

 —OH, or
when A is:

and B—C is:

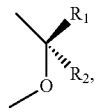

wherein R is H or alkyl, wherein $R_1$ is H and $R_2$ is alkoxyl, or $R_2$ is H and $R_1$ is alkoxyl, and wherein $R_3$ is H and $R_4$ is alkoxyl, or $R_4$ is H and $R_3$ is alkoxyl; or a pharmaceutically acceptable salt thereof. In some embodiments, R is H or $C_1$ to $C_5$ alkyl, wherein $R_1$ is H and $R_2$ is $C_1$ to $C_5$ alkoxyl, or $R_2$ is H and $R_1$ is $C_1$ to $C_5$ alkoxyl, and wherein $R_3$ is H and $R_4$ is $C_1$ to $C_5$ alkoxyl, or $R_4$ is H and $R_3$ is $C_1$ to $C_5$ alkoxyl.

In some embodiments of the composition of the invention, the compound has the following structure:

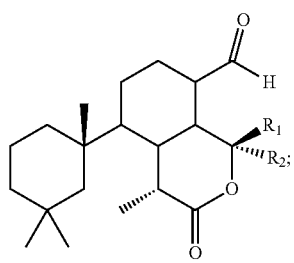

(II)

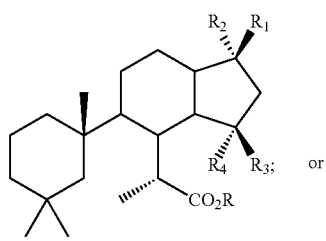

(III)

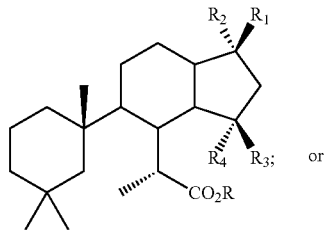

(IV)

wherein R is H or alkyl, wherein $R_1$ is H and $R_2$ is alkoxyl, or $R_2$ is H and $R_1$ is alkoxyl, and wherein $R_3$ is H and $R_4$ is alkoxyl, or $R_4$ is H and $R_3$ is alkoxyl; or a pharmaceutically acceptable salt thereof. In some embodiments, R is H or $C_1$ to $C_5$ alkyl, wherein $R_1$ is H and $R_2$ is $C_1$ to $C_5$ alkoxyl, or $R_2$ is H and $R_1$ is $C_1$ to $C_5$ alkoxyl, and wherein $R_3$ is H and $R_4$ is $C_1$ to $C_5$ alkoxyl, or $R_4$ is H and $R_3$ is $C_1$ to $C_5$ alkoxyl.

In some embodiments, the compound has a structure shown in FIG. 1, or a pharmaceutically acceptable salt thereof. In other embodiments, the compound is not a compound having a structure shown in FIG. 1 or a pharmaceutically acceptable salt thereof.

In some embodiments of the composition of the invention, the compound has the following structure:

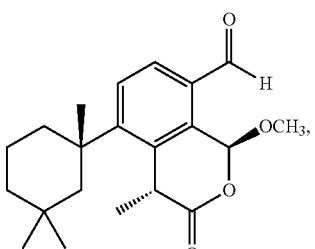

Membranolide B

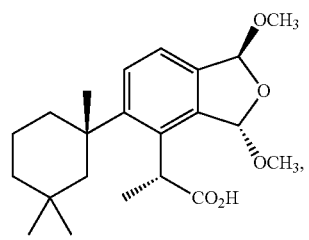

Membranolide C

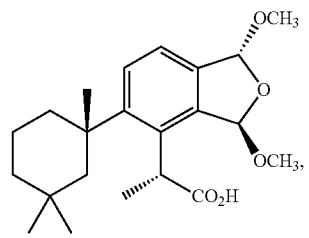

Membranolide D

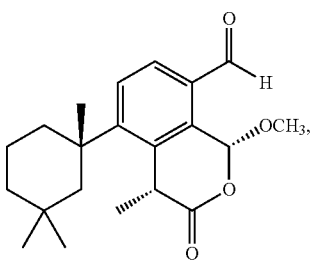

Membranolide E

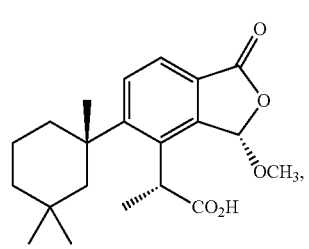

Membranolide F

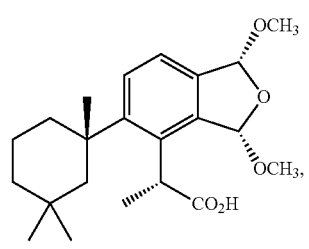

Membranolide G

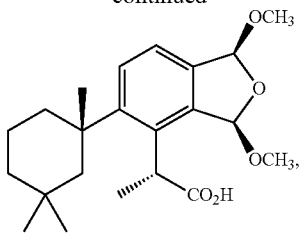

Membranolide H

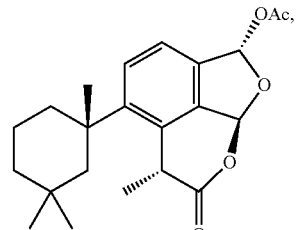

Apylsulphurin (1)

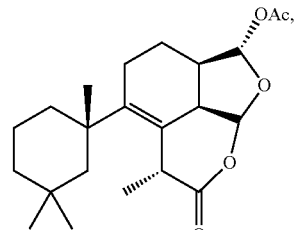

Tetrahydroaplysulphurin (2)

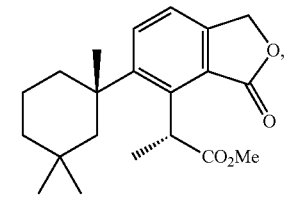

Membranolide A (3)

or a pharmaceutically acceptable salt thereof

In some embodiments of the composition of the invention, the anti-*Leishmania* agent is an antimonial, amphotericin B, miltefosine, pentamidine, aminoglycoside-amino-cyclitol antibiotic, azole, 4-methyl-6-methoxy-8-aminoquinoline, or nucleoside analogue, or a combination of two or more of the foregoing.

Another aspect of the invention is a method for treatment of leishmaniasis, comprising administering an effective amount of a compound having the following structure to the subject:

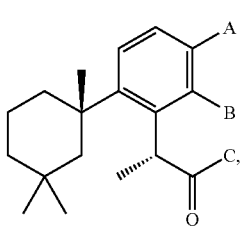

(I)

wherein A-B—C is:

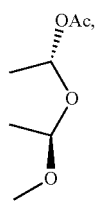

or
when A-B is:

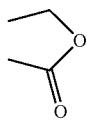

and C is:

or
when A-B is

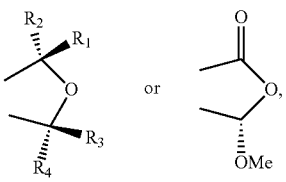

and C is:

or
when A is:

and B—C is:

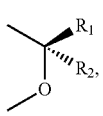

wherein R is H or alkyl, wherein $R_1$ is H and $R_2$ is alkoxyl, or $R_2$ is H and $R_1$ is alkoxyl, and wherein $R_3$ is H and $R_4$ is alkoxyl, or $R_4$ is H and $R_3$ is alkoxyl; or a pharmaceutically acceptable salt thereof. In some embodiments, R is H or $C_1$ to $C_5$ alkyl, wherein $R_1$ is H and $R_2$ is $C_1$ to $C_5$ alkoxyl, or $R_2$ is H and $R_1$ is $C_1$ to $C_5$ alkoxyl, and wherein $R_3$ is H and $R_4$ is $C_1$ to $C_5$ alkoxyl, or $R_4$ is H and $R_3$ is $C_1$ to $C_5$ alkoxyl.

In some embodiments of the treatment method, the compound has the following structure:

(II)

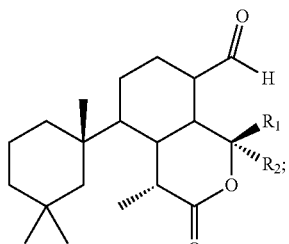

(III)

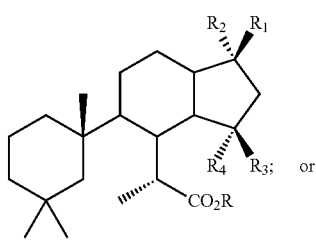

or (IV)

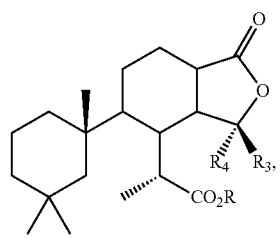

wherein R is H or alkyl, wherein $R_1$ is H and $R_2$ is alkoxyl, or $R_2$ is H and $R_1$ is alkoxyl, and wherein $R_3$ is H and $R_4$ is alkoxyl, or $R_4$ is H and $R_3$ is alkoxyl; or a pharmaceutically acceptable salt thereof. In some embodiments, R is H or $C_1$ to $C_5$ alkyl, wherein $R_1$ is H and $R_2$ is $C_1$ to $C_5$ alkoxyl, or $R_2$ is H and $R_1$ is $C_1$ to $C_5$ alkoxyl, and wherein $R_3$ is H and $R_4$ is $C_1$ to $C_5$ alkoxyl, or $R_4$ is H and $R_3$ is $C_1$ to $C_5$ alkoxyl.

In some embodiments, the compound has a structure shown in FIG. 1, or a pharmaceutically acceptable salt thereof. In other embodiments, the compound is not a compound having a structure shown in FIG. 1 or a pharmaceutically acceptable salt thereof.

In some embodiments of the treatment method, the compound has the following structure:

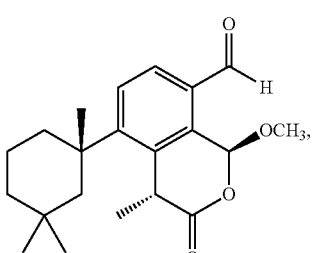

Membranolide B

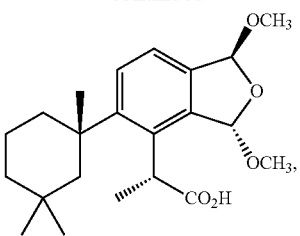

Membranolide C

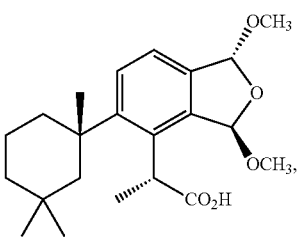

Membranolide D

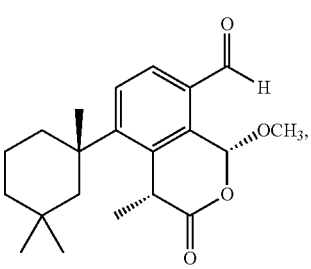

Membranolide E

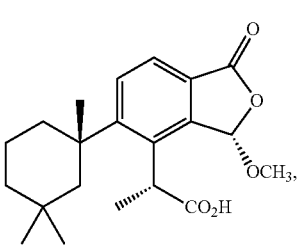

Membranolide F

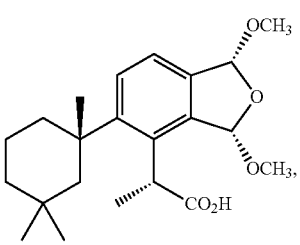

Membranolide G

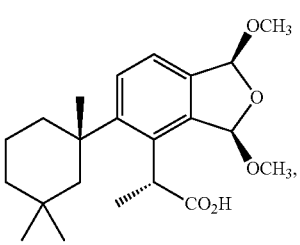

Membranolide H

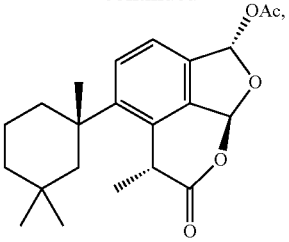

Apylsulphurin (1)

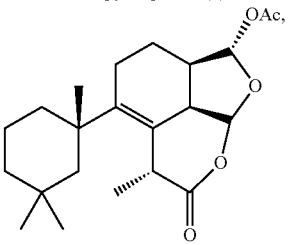

Tetrahydroaplysulphurin (2)

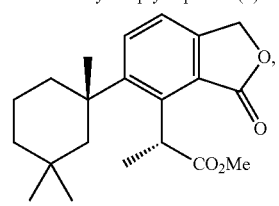

Membranolide A (3)

or a pharmaceutically acceptable salt thereof.

In some embodiments, the causative agent of the leishmaniasis is *L. aethiopica, L. amazonensis, L. arabica, L. braziliensis, L. dovani (L. dovani dovani, L. dovani infantum, L. dovani chagasi), L. enrietti, L. gerbilli, L. hertigi, L. infantum, L. killicki, L. major, L. martiniquensis, L. mexicana (L. mexicana mexicana, L. mexicana amazonensis, L. mexicana pifanoi), L. peruviana, L. siamensis, L. tropica*, or *L. turanica*.

Another aspect of the invention concerns a method for controlling *Leishmania* spp. parasites, comprising applying an effective amount of a compound disclosed herein to a *Leishmania* parasite, or to the situs of a *Leishmania* parasite, in vitro or in vivo.

In some embodiments, the *Leishmania* parasite is *L. aethiopica, L. amazonensis, L. arabica, L. braziliensis, L. dovani (L. dovani dovani, L. dovani infantum, L. dovani chagasi), L. enrietti, L. gerbilli, L. hertigi, L. infantum, L. killicki, L. major, L. martiniquensis, L. mexicana (L. mexicana mexicana, L. mexicana amazonensis, L. mexicana pifanoi), L. peruviana, L. siamensis, L. tropica*, or *L. turanica*.

In some embodiments of the *Leishmania* spp. control method, the compound has the following structure to the subject:

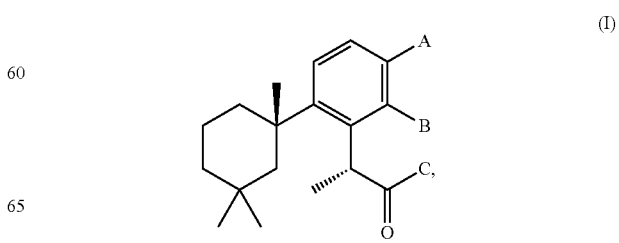

(I)

wherein A-B—C is:

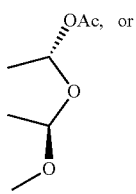

or
when A-B is:

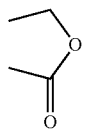

and C is:

 —OMe, or
when A-B is

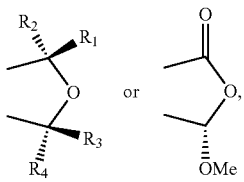

and C is:

 —OH, or
when A is:

and B—C is:

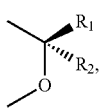

wherein R is H or alkyl, wherein $R_1$ is H and $R_2$ is alkoxyl, or $R_2$ is H and $R_1$ is alkoxyl, and wherein $R_3$ is H and $R_4$ is alkoxyl, or $R_4$ is H and $R_3$ is alkoxyl; or a pharmaceutically acceptable salt thereof. In some embodiments, R is H or $C_1$ to $C_5$ alkyl, wherein $R_1$ is H and $R_2$ is $C_1$ to $C_5$ alkoxyl, or $R_2$ is H and $R_1$ is $C_1$ to $C_5$ alkoxyl, and wherein $R_3$ is H and $R_4$ is $C_1$ to $C_5$ alkoxyl, or $R_4$ is H and $R_3$ is $C_1$ to $C_5$ alkoxyl.

In some embodiments of the *Leishmania* spp. control method, the compound has the following structure:

(II)

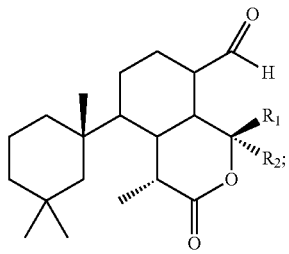

(III)

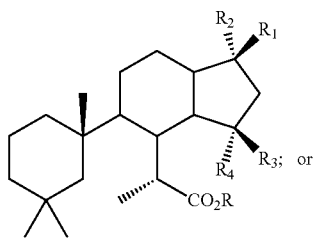

(IV)

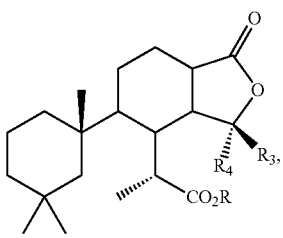

wherein R is H or alkyl, wherein $R_1$ is H and $R_2$ is alkoxyl, or $R_2$ is H and $R_1$ is alkoxyl, and wherein $R_3$ is H and $R_4$ is alkoxyl, or $R_4$ is H and $R_3$ is alkoxyl; or a pharmaceutically acceptable salt thereof. In some embodiments, R is H or $C_1$ to $C_5$ alkyl, wherein $R_1$ is H and $R_2$ is $C_1$ to $C_5$ alkoxyl, or $R_2$ is H and $R_1$ is $C_1$ to $C_5$ alkoxyl, and wherein $R_3$ is H and $R_4$ is $C_1$ to $C_5$ alkoxyl, or $R_4$ is H and $R_3$ is $C_1$ to $C_5$ alkoxyl.

In some embodiments, the compound has a structure shown in FIG. 1, or a pharmaceutically acceptable salt thereof. In other embodiments, the compound is not a compound having a structure shown in FIG. 1 or a pharmaceutically acceptable salt thereof.

In some embodiments of the *Leishmania* spp. control method, the compound has the following structure:

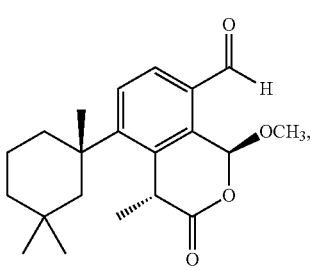

Membranolide B

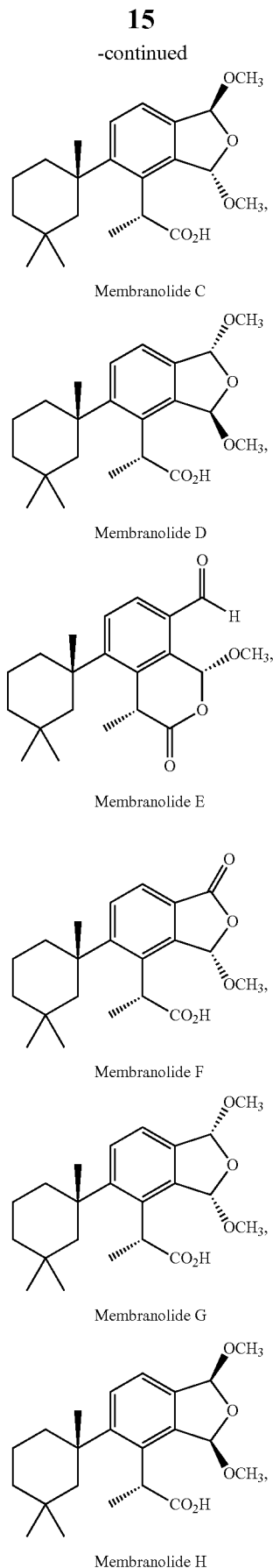

Membranolide C

Membranolide D

Membranolide E

Membranolide F

Membranolide G

Membranolide H

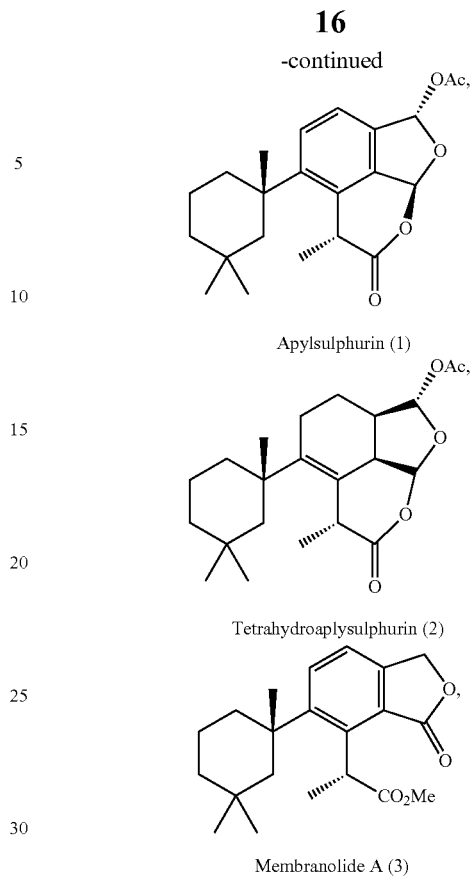

Apylsulphurin (1)

Tetrahydroaplysulphurin (2)

Membranolide A (3)

or a pharmaceutically acceptable salt thereof.

In some embodiments, the *Leishmania* parasite is *L. aethiopica, L. amazonensis, L. arabica, L. braziliensis, L. dovani* (*L. dovani dovani, L. dovani infantum, L. dovani chagasi*), *L. enrietti, L. gerbilli, L. hertigi, L. infantum, L. killicki, L. major, L. martiniquensis, L. mexicana* (*L. mexicana mexicana, L. mexicana amazonensis, L. mexicana pifanoi*), *L. peruviana, L. siamensis, L. tropica,* or *L. turanica*.

Figure 3:
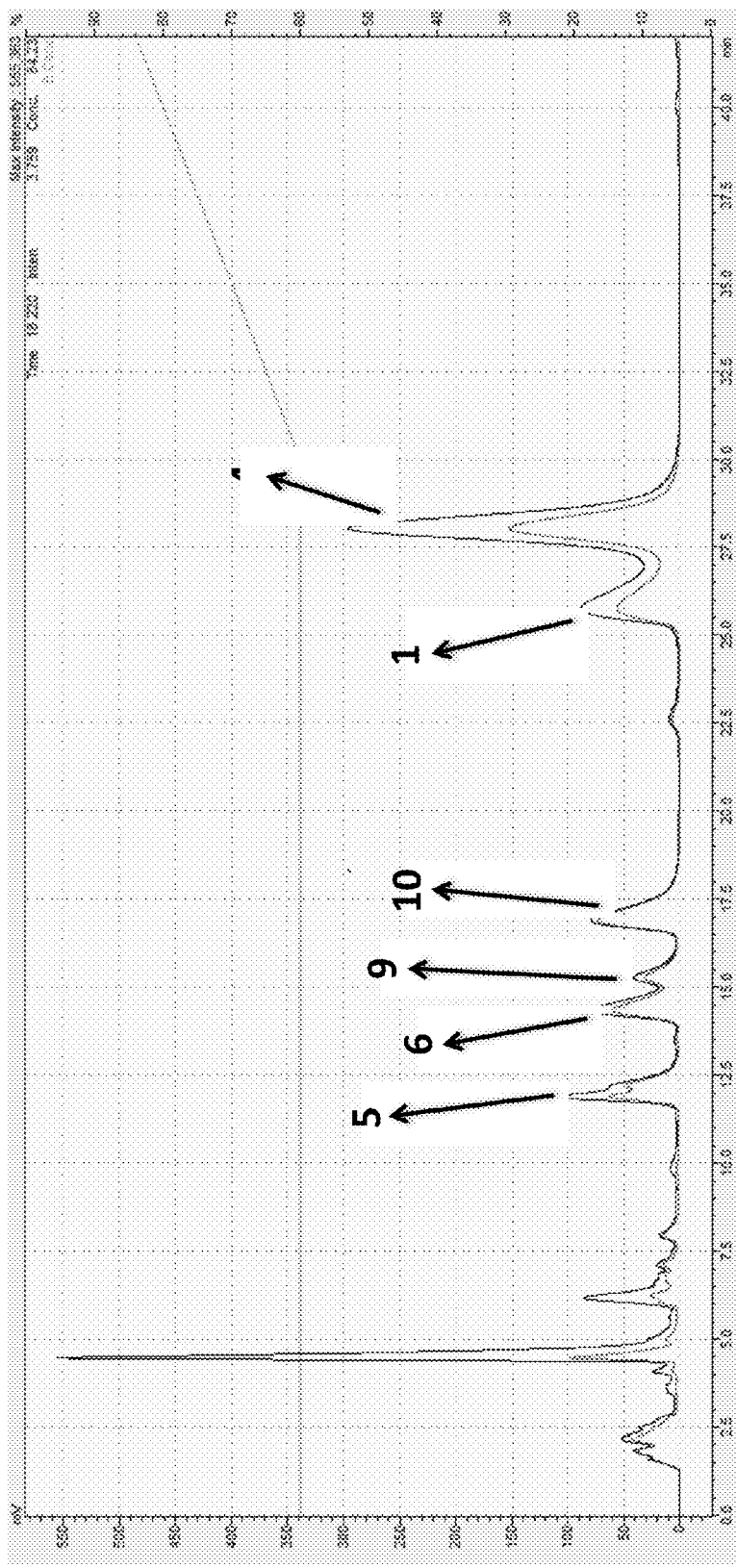
FIG. 3 shows a high-performance liquid chromatography (HPLC) chromatogram displaying UV peaks at 254 nm (black) and 280 nm (pink) of the isolated compounds: membranolide E (5), membranolide C (6), membranolide H (9), membranolide F (10), membranolide B (4), and starting material, aplysulphurin (1).
Figure 4:
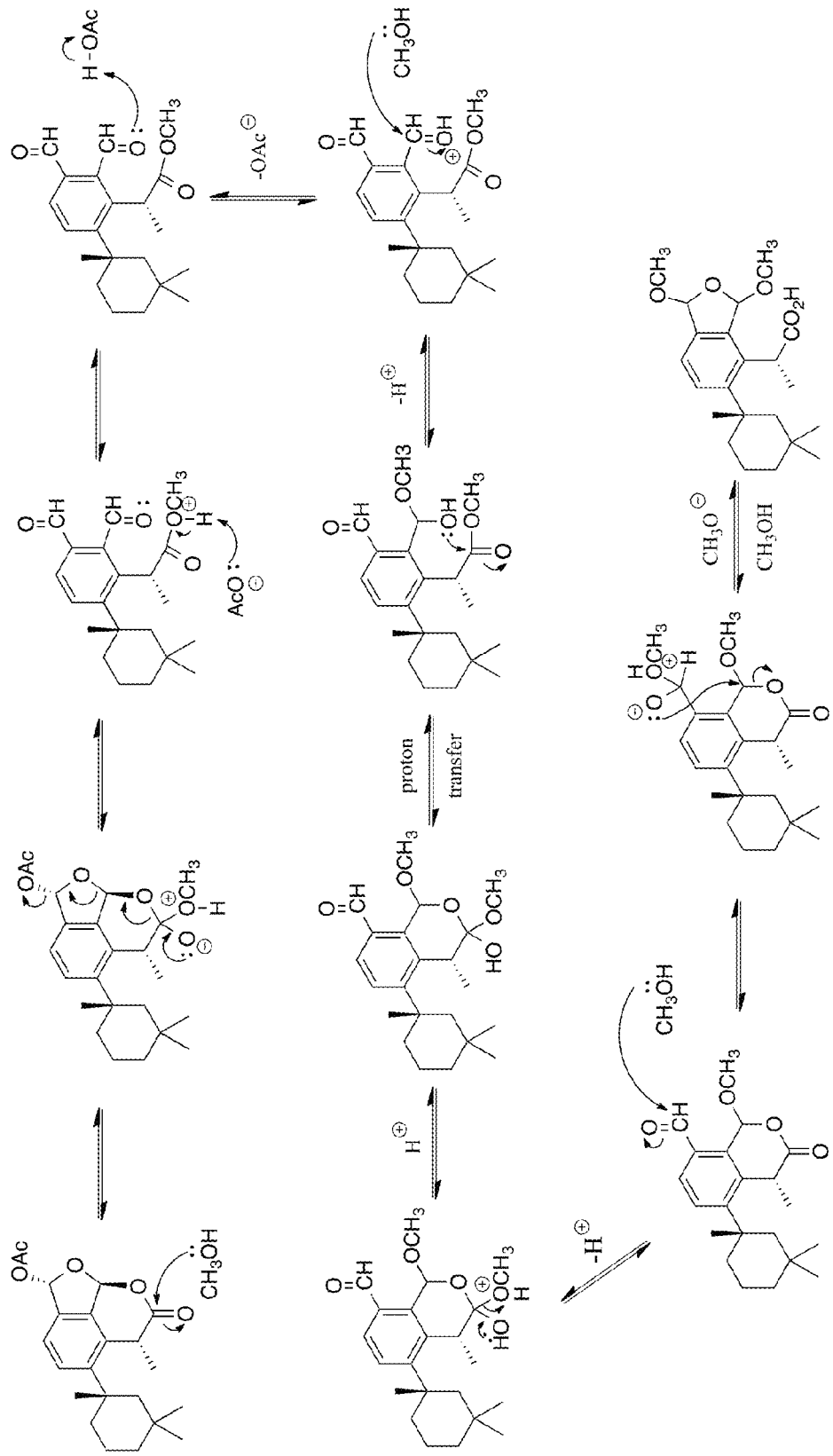
FIG. 4 shows a proposed mechanism for the formation of the methoxy analogues from aplysulphurin.

Example 2 describes isolation of compounds of the invention. Aplysulphurin was dissolved in methanol and the resulting material was purified with reverse-phase HPLC. FIG. 3 shows an HPLC chromatogram displaying UV peaks at 254 nm (black) and 280 nm (pink) of the isolated compounds: membranolides E (5), C (6), H (9), F (10), B (4), and starting material, aplysulphurin (1). FIG. 4 shows the proposed mechanism for the formation of the methoxy analogues from aplysulphurin. After degradation, recovery of aplysulphurin was 60%, membranolide B was the major product isolated in a 21% yield, all other compounds were purified with <5% yield. Table 1 shows the results of structure-activity relationship (SAR) studies for anti-leishmanial activity.

The invention includes isomers, racemates or racemic mixtures thereof, and analogs of membranolide compounds disclosed herein.

As used herein, the term "analogs" refers to compounds which are substantially the same as another compound but which may have been modified by, for example, adding side groups, oxidation or reduction of the parent structure. Analogs of the membranolide compounds can be readily prepared using commonly known standard reactions. These standard reactions include, but are not limited to, hydrogenation, alkylation, acetylation, and acidification reactions.

Chemical modifications can be accomplished by those skilled in the art by protecting all functional groups present in the molecule and deprotecting them after carrying out the desired reactions using standard procedures known in the scientific literature (Greene, T. W. and Wuts, P. G. M. "Protective Groups in Organic Synthesis" John Wiley & Sons, Inc. New York. 3rd Ed. pg. 819, 1999; Honda, T. et al. *Bioorg. Med. Chem. Lett.,* 1997, 7:1623-1628; Honda, T. et al. *Bioorg. Med. Chem. Lett.,* 1998, 8:2711-2714; Konoike, T. et al. *J. Org. Chem.,* 1997, 62:960-966; Honda, T. et al. *J. Med. Chem.,* 2000, 43:4233-4246; each of which are hereby incorporated herein by reference in their entirety).

The subject invention also concerns methods for isolating and purifying a compound of the present invention. In one embodiment, the method comprises subjecting *D. membranosa* sponge material to solvent extraction (e.g., alcoholysis); removing said solvent to provide an extract; and fractionating said extract to isolate the membranolides. Examples of solvents that may be used for extraction include, but are not limited to, alcohols such as methanol, ethanol, propanol, butanol, and pentanol.

The subject invention also concerns methods for synthesizing a compound of the present invention.

Treatment of Leishmaniasis and Control of *Leishmania* Spp. Parasites

An aspect of the invention is a method for treatment of leishmaniasis, comprising administering an effective amount of a compound disclosed herein, including those having a structure shown in FIG. 1, formula (I), formula (II), formula (III), and formula (IV). The subject may be a human or a non-human animal of any age and gender. In some embodiments, the subject is a human or non-human mammal. In some embodiments, the subject is a canine. Many mammals are potential host reservoirs, including rodents, foxes, and jackals, tree sloths, and dogs. Close human interactions with domesticated dogs are believed to be a significant source of human infection. Vanloubbeeck and Jones, *Ann. NY. Acad. Sci.,* 2004, 1026:267-272.

The subject may be suffering from one or more conditions that are known to co-occur with leishmaniasis, such as HIV infection. The subject may or may not be immunocompromised.

The compound may be administered to a subject having leishmaniasis at the time of administration (as therapy), or administered when the subject does not currently have leishmaniasis, before or after exposure (as prophylaxis, to prevent or delay the onset of the disease). The subject may have previously suffered from leishmaniasis.

In some embodiments in which the subject has leishmaniasis and the compound is administered as therapy, the subject may have previously undergone a different treatment for the leishmaniasis. The leishmaniasis may be a form that is resistant to one or more other treatments.

The compound may be administered locally, to a site of leishmaniasis infection or *leishmania* parasite, or systemically.

At least nineteen species of *Leishmania* are potentially capable of infecting humans, and depending on the species of *Leishmania* involved and factors peculiar to the host (genetic, immunological, etc.), they are the source of very diverse clinical manifestations. Some of the most significant include *L. major, L. infantum, L. donovani, L. mexicana, L. hraziliensis, L. chagasi,* and *L. amazonensis*. In some embodiments, the *Leishmania* parasite is *L. aethiopica, L. amazonensis, L. arabica, L. braziliensis, L. dovani* (*L. dovani dovani, L. dovani infantum, L. dovani chagasi*), *L. enrietti, L. gerbilli, L. hertigi, L. infantum, L. killicki, L. major, L. martiniquensis, L. mexicana* (*L. mexicana mexicana, L. mexicana amazonensis, L. mexicana pifanoi*), *L. peruviana, L. siamensis, L. tropica,* or *L. turanica.*

Another aspect of the invention concerns a method for controlling *Leishmania* spp. parasites, comprising applying (contacting) an effective amount of a compound disclosed herein to a *Leishmania* parasite, or to the situs of a *Leishmania* parasite or Leishmanial infection, in vitro or in vivo. Preferably, the effective amount is an anti-Leishmanial effective amount.

In some embodiments, the *Leishmania* parasite is *L. aethiopica, L. amazonensis, L. arabica, L. braziliensis, L. dovani* (*L. dovani dovani, L. dovani infantum, L. dovani chagasi*), *L. enrietti, L. gerbilli, L. hertigi, L. infantum, L. killicki, L. major, L. martiniquensis, L. mexicana* (*L. mexicana mexicana, L. mexicana amazonensis, L. mexicana pifanoi*), *L. peruviana, L. siamensis, L. tropica,* or *L. turanica.*

Like *Trypanosoma brucei* and *T. cruzi, Leishmania* are highly adaptive and have several life stages. *Leishmania* can exist in two forms: a mobile flagellated form called a promastigote, and a smaller non-mobile, non-flagellated intracellular form, the amastigote. The promastigotes are found in the gut of the sandfly, while amastigotes infect humans and other vertebrate hosts. The parasite is transmitted by the bite of a sandfly. The sandfly is difficult vector to control. The *Leishmania* spp. parasite can be controlled by applying the compound to the parasite or its situs at any life stage. For in vivo embodiments, an effective amount of one or more of the compounds disclosed herein are administered to the subject as with the method of treatment.

Within the insect, amastigotes transform in to the promastigote form. The promastigotes then migrate to the midgut of the fly, where they live extracellularly and multiply by binary fission. Promastigotes then move forward to the esophagus and the salivary glands of the insect. When the sandfly next feeds on a mammalian host, the *Leishmania* promastigotes are transferred to the host.

Once in the host, the promastigotes are taken up by the macrophages where they revert to the amastigote form. Amastigotes multiply inside the macrophages, eventually leading to the lysis of the macrophages (Vanloubbeeck and Jones, *Ann. NY. Acad. Sci.,* 2004, 1026:267-72). The released amastigotes are taken up by additional macrophages and the cycle continues. Ultimately, if untreated, all the organs containing macrophages and phagocytes are infected, particularly the spleen, liver and bone marrow.

Leishmaniasis develops mainly into three distinct clinical forms: cutaneous, mucocutaneous, and visceral depending on whether the parasites affect the mononuclear phagocytic system of the dermis, the mucous membranes, or the internal organs. The cutaneous lesion can remain localized at the point of inoculation of the parasite and correspond to a benign form with spontaneous healing. Besides this form, more serious pathologies exist, caused by disseminated cutaneous leishmaniasis and mucocutaneous leishmaniasis.

The most serious, and often fatal leishmaniasis, if untreated, is visceral leishmaniasis (kala azar), with symptoms including fever, malaise, weight loss, anemia, swelling of the spleen, liver and lymph nodes. Primarily affected organs are the liver, spleen, bone marrow and other elements of the reticuloendothelial system, which are enlarged due to the infected macrophages. After a few months to a year, the subject becomes emaciated and exhausted. Death is generally due to other concurrent infections. The visceral form of leishmaniasis can also incubate for months or years before becoming clinically apparent. Furthermore, the disease can manifest itself in immunocompromised subjects years after exposure in endemic regions. Because of the reduced ability of such subjects to resist disease, treatment modalities for this form of the disease are most urgently required.

The most common manifestation is cutaneous leishmaniasis, resulting in multiple skin lesions and scarring. Mucocutaneous leishmaniasis begins with skin ulcers that spread and cause massive tissue destruction, especially of the nose and mouth and leaves victims horribly disfigure (Vanloubbeeck and Jones, *Ann. N.Y. Acad. Sci.*, 2004, 1026:267-72). Drug therapy is limited, and evidence of drug resistance has further narrowed the pool of candidate drugs (Murray, *Am. J. Trop. Med. Hyg.*, 2004, 71(6):787-94; Croft et al., *Clinical Microbiology Reviews*, 2006, 19(1):111-126).

In the treatment and control methods described herein, the compound(s) disclosed herein may be administered to the subject or applied to the *Leishmania* spp. parasite or situs by itself as a mono-treatment or one or more additional agents may be used and administered or applied before, during, and/or after administration or application of one or more compounds disclosed herein as a combination treatment or regimen. If administered or applied during simultaneously, the additional agent(s) may be administered or applied in the same composition or a separate composition from that of the compound(s) disclosed herein. For example, one or more other agents useful in treating leishmaniasis or controlling *Leishmania* spp. parasites may be administered or applied before, during, and/or after administration or application of a compound disclosed herein, such as an antimonial (e.g., pentavalent antimonials such as sodium stibogluconate, meglumine antimonite), amphotericin B (e.g., conventional or liposomal), miltefosine (hexadecylphosphocholine), pentamidine, aminoglycoside-amino-cyclitol antibiotic (e.g., paromycin), azole (e.g., ketoconazole, itraconazole, fluconazole), 4-methyl-6-methoxy-8-aminoquinoline (e.g., sitamaquine), or nucleoside analogue (such as a pyrazolopyrimidine, e.g., allopurinol).

One or more additional agents effective for treatment of disorders that can co-occur with leishmaniasis may be administered (e.g., for treatment of HIV).

In the treatment method of the invention, optionally, the method may include determining whether the subject has leishmaniasis prior to administration of one or more compounds disclosed herein. In in vivo embodiments of the *Leishmania* spp. parasite control method of the invention, the method may include determining whether a *Leishmania* spp. parasite is present.

Various laboratory methods can be used to diagnose leishmaniasis—to detect the parasite as well as to identify the *Leishmania* species (type). Some of the methods are available only in laboratories. Non-invasive serological diagnostic methods with high sensitivity and specificity are available, such as direct agglutination test (DAT), K39 strip test, and KAtex (urine dipstick; Kalon Biological, UK) (Boelaert et al., *Am. J. Trop. Med. Hyg.*, 2004, 70:72-77; Guerin et al., *Lancet Infect. Dis.*, 2002, ii:494-501; Goswami et al., *J. Assoc. Physicians India*, 2003, 51:759-61).

Tissue specimens, such as from skin sores (for cutaneous leishmaniasis) or from bone marrow (for visceral leishmaniasis), can be examined for the parasite under a microscope, in special cultures, for example. Blood tests that detect antibody (an immune response) to the parasite can be used for cases of visceral leishmaniasis; tests to look for the parasite itself usually also are done (See Singh S, *Indian J Med Res*, March 2006, 123:311-330, incorporated herein by reference in its entirety). Antibody levels do not necessarily indicate active infection, vary between individuals, and are not useful in cases of HIV/visceral leishmaniasis co-infection. Parasite antigen detection is more important for monitoring treatment response (see, for example, Rijal et al., *Nepal. Trop. Med. Int. Health*, 2004, 9:724-729; Riera et al., *Eur. J. Clin. Microbiol. Infect. Dis.*, 2004, 23(12):899-904).

The term "subject" includes human. A subject in need of treatment includes a human subject in need of treatment against *Leishmania* spp. parasites. Thus, methods of treating a mammal other than human (veterinary treatments) against *Leishmania* parasites are also within the scope of our inventions, and in particular canines.

A subject in need of treatment may be diagnosed by testing and by physical examination. Testing includes serological tests, immunoassays and polymerase chain reaction (PCR) methods to diagnose for the presence of *Leishmania* spp. parasites infection in an individual. The testing is sometimes performed in tandem. Serological testing of blood samples from an individual can yield negative and positive sero results. A so-called sero-positive result is indicative of infection. So-called sero-negative results may or may not indicate the absence of infection. The primary limitation of this technique revolves around interpretation of a positive titer, which may only indicate exposure to the parasite as opposed to active infection. However, due to the disease progression more than a single test with a single sero-negative result is preferred. PCR methods can be used in determining a patient in need of treatment. A more reliable diagnostic test relies on demonstration of *Leishmania* spp. parasites either cytologically or histopathologically, in stained preparations of bone marrow, lymph node, spleen, skin or other tissues and organs (skeletal muscle, peripheral nerves, renal interstitium, and synovial membranes. *Leishmania* parasites most commonly reside in macrophages, but have been observed in other cell lines including neutrophils, eosinophilis, endothelial cells and fibroblasts. While microscopic visualization of parasites provides a definitive diagnosis, this technique may be only approximately 60% effective for bone marrow samples and less effective for lymph node specimens, making it less sensitive than other testing strategies.

Diagnosis of a subject in the acute phase of leishmaniasis disease who is in need of treatment may include physical examination. The acute stage may extend for a few weeks or months following initial infection. Many symptoms may not be unique to leishmaniasis disease.

In some embodiments, the methods of the invention include determining the presence of leishmaniasis, or the presence of *Leishmania* spp. in a subject, by direct microscopic examination (e.g., amastigote forms (LD bodies) seen intracellularly in monocytes or macrophages on microscopic examination of Giemsa-stained blood or aspirates from lymph nodes, bone marrow, or spleen), antigen detection (e.g., agglutination test, gel-diffusion immunoelectrophoresis, complement-fixation test, indirect haemagglutination test, counter-current immunoelectrophoresis, indirect fluorescence antibody (IFA) test, or antibody-detection test (e.g., direct agglutination test (DAT), or rK39 immunochromatographic test (ICT)), molecular diagnosis, or serological method.

Steps may be taken to monitor treatment (e.g., dosing), symptoms, treatment response, and status of the leishmaniasis or presence or absence of *Leishmania* parasites over time after administration or application of the compound has been initiated.

Compositions

Another aspect of this invention is compositions that contain an effective amount of a subject compound, or a pharmaceutically acceptable salt thereof, and a pharmaceutically acceptable carrier. In some embodiments, the composition is a "safe and effective amount". As used herein, "safe and effective amount" means an amount of the subject compound sufficient to significantly induce a positive modification in the condition to be treated, but low enough to avoid serious side effects (at a reasonable benefit/risk ratio), within the scope of sound medical judgment. A safe and effective amount of the subject compound will vary with the age and physical condition of the subject being treated, the severity of the condition, the duration of the treatment, the nature of concurrent therapy, the particular pharmaceutically-acceptable carrier utilized, and like factors within the knowledge and expertise of the attending physician.

Preparing a dosage form is within the purview of the skilled artisan. Examples are provided for the skilled artisan, but are non-limiting, and it is contemplated that the skilled artisan can prepare variations of the compositions claimed.

In addition to the subject compound, the compositions of this invention contain a pharmaceutically acceptable carrier. The term "pharmaceutically acceptable carrier," as used herein, means one or more compatible solid or liquid filler diluents or encapsulating substances that are suitable for administration to a mammal. The term "compatible", as used herein, means that the components of the composition are capable of being commingled with the subject compound, and with each other, in a manner such that any interactions do not substantially reduce the efficacy of the composition under ordinary use situations. Preferably, when liquid dose forms are used, the compounds disclosed are soluble in the components of the composition. Pharmaceutically acceptable carriers are of sufficiently high purity and sufficiently low toxicity to render them suitable for administration to the subject being treated.

Some examples of substances that can serve as pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the Tweens; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically acceptable carrier to be used in conjunction with the compound is basically determined by the way the compound is to be administered. If the compound is to be injected, the preferred pharmaceutically acceptable carrier is sterile, physiological saline, with a blood-compatible suspending agent, the pH of which has been adjusted to about 7.4 for a human subject.

If the mode of administering the compound or composition is perorally, the preferred unit dosage form is therefore tablets, capsules, lozenges, chewable tablets, and the like. Such unit dosage forms contain a safe and effective amount of the subject compound, which is preferably from about 0.01 mg to about 350 mg, more preferably from about 0.1 mg to about 35 mg, based on a 70 kg person. The pharmaceutically acceptable carrier, suitable for the preparation of unit dosage forms for peroral administration, are well-known in the art. Tablets typically contain conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically contain one or more solid diluents disclosed above. The selection of carrier components depends on secondary considerations like taste, cost, and shelf stability, which are not critical for the purposes of this invention, and can be readily made by a person skilled in the art.

Peroral compounds and compositions also include liquid solutions, emulsions, suspensions, and the like. The pharmaceutically acceptable carriers suitable for preparation of such compositions are well known in the art. Such liquid oral compositions preferably contain from about 0.001% to about 5% of the subject compound, more preferably from about 0.01% to about 0.5%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth and sodium alginate; typical wetting agents include lecithin and polysorbate 80; and typical preservatives include methyl paraben and sodium benzoate. Peroral liquid compositions can also contain one or more components such as sweeteners, flavoring agents and colorants disclosed above.

Other compositions useful for attaining systemic delivery of the subject compounds and compositions include sublingual and buccal dosage forms. Such compositions typically contain one or more of soluble filler substances such as sucrose, sorbitol and mannitol; and binders such as *acacia*, microcrystalline cellulose, carboxymethyl cellulose and hydroxypropyl methyl cellulose. Glidants, lubricants, sweeteners, colorants, antioxidants and flavoring agents disclosed above can also be included.

Compositions can also be used to deliver the compound to the site where activity is desired: intranasal doses for nasal decongestion, inhalants for asthma, and eye drops, gels and creams for ocular disorders.

Some compositions of this invention include solutions or emulsions, preferably aqueous solutions or emulsions containing a safe and effective amount of a subject compound intended for topical intranasal administration. Such compositions preferably contain from about 0.001% to about 25% of a subject compound, more preferably from about 0.01% to about 10%. Similar compositions are preferred for systemic delivery of subject compounds by the intranasal route. Compositions intended to deliver the compound systemically by intranasal dosing preferably contain similar amounts of a subject compound as are determined to be safe and effective by peroral or parenteral administration. Such compositions used for intranasal dosing also typically include safe and effective amounts of preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfate and others; aromatic agents; viscosity adjustors, such as polymers, including cellulose and derivatives thereof, and polyvinyl alcohol and acids and bases to adjust the pH of these aqueous compositions as needed. The compositions can also contain local anesthetics or other actives. These compositions can be used as sprays, mists, drops, and the like.

Other compositions of this invention include aqueous solutions, suspensions, and dry powders containing a safe and effective amount of a subject compound intended for atomization and inhalation administration. Such compositions typically contain from about 0.1% to about 50% of a subject compound, more preferably from about 1% to about 20%; of course, the amount can be altered to fit the circumstance of the subject contemplated and the package. Such compositions are typically contained in a container with attached devices for atomization. Such compositions also typically include propellants such as chlorofluorocarbons 12/11 and 12/114, and more environmentally friendly fluorocarbons, or other nontoxic volatiles; solvents such as water, glycerol and ethanol, these include co-solvents as needed to solvate or suspend the active; stabilizers such as ascorbic acid, sodium metabisulfite; preservatives such as cetylpyridinium chloride and benzalkonium chloride: tonicity adjustors such as sodium chloride; buffers; and flavoring agents such as sodium saccharin. In some embodiments, the compounds and methods are administered to the subject or applied in vivo systemically by intravenous delivery.

Other compositions of this invention include aqueous solutions containing a safe and effective amount of a subject compound intended for topical intraocular administration. Such compositions preferably contain from about 0.0001% to about 5% of a subject compound, more preferably from about 0.01% to about 0.5%. Such compositions also typically include one or more of preservatives, such as benzalkonium chloride, thimerosal, phenylmercuric acetate; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases can be used to adjust the pH of these formulations as needed.

Other compositions of the invention useful for peroral administration include solids, such as tablets and capsules, and liquids, such as solutions, suspensions and emulsions (preferably in soft gelatin capsules), containing a safe and effective amount of a subject compound. Such compositions typically contain from about 0.01 mg to about 350 mg per dose, more preferably from about 0.1 mg to about 35 mg per dose. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Pharmaceutically acceptable salts include but are not limited to salts of acidic or basic groups that can be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, that is, salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate salts. Compounds that include an amino moiety can form pharmaceutically or cosmetically acceptable salts with various amino acids, in addition to the acids mentioned above. Compounds that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts. Prodrugs of the compounds disclosed herein may be used.

Any of the compositions of this invention can, optionally, include other biologically active agents, such as other agents for control of *Leishmania* spp. parasites or for treatment of leishmaniasis (therapy or prophylaxis), or agents effective for treatment of disorders that can co-occur with leishmaniasis, such as HIV. Examples of agents useful in treating leishmaniasis or controlling *Leishmania* spp. parasites an antimonial (e.g., pentavalent antimonials such as sodium stibogluconate, meglumine antimonite), amphotericin B (e.g., conventional or liposomal), miltefosine (hexadecylphosphocholine), pentamidine, aminoglycoside-amino-cyclitol antibiotic (e.g., paromycin), azole (e.g., ketoconazole, itraconazole, fluconazole), 4-methyl-6-methoxy-8-aminoquinoline (e.g., sitamaquine), and nucleoside analogue (such as a pyrazolopyrimidine, e.g., allopurinol).

The subject invention also concerns kits, comprising in one or more containers a compound or composition of the invention. In a specific embodiment, a kit of the invention comprises one or more compounds having the structure of formula (I), or a pharmaceutically acceptable salt thereof. In some embodiments, the compound has the structure of formula (II), (III), or (IV), or a pharmaceutically acceptable salt thereof. In some embodiments, the compound is aplysulphurin (compound 1), tetrahydroaplysuphurin (compound 2), membranolide A (compound 3), membranolide B (compound 4), membranolide C (compound 6), membranolide D (compound 7), membranolide E (compound 5), membranolide F (compound 10), or membranolide G (compound 8), or membranolide (H) (compound 9), having a structure shown in FIG. 1, or a pharmaceutically acceptable salt thereof. In one embodiment, a kit further comprises a pharmaceutically acceptable carrier, such as a diluent. In another embodiment, a kit further comprises an antitumor or anticancer compound.

Definitions

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the terms "a" and "an" preceding an element or component of the invention are intended to be nonrestrictive regarding the number of instances, i.e., occurrences of the element or component. Therefore, "a" or "an" should be read to include one or at least one, and the singular word form of the element or component also includes the plural unless the number is obviously meant to be singular.

As used herein, the terms "administration" and "administering" are used to describe the process in which one or more compounds disclosed herein (such as aplysulphurin (compound 1), tetrahydroaplysuphurin (compound 2), membranolide A (compound 3), membranolide B (compound 4), membranolide C (compound 6), membranolide D (compound 7), membranolide E (compound 5), membranolide F (compound 10), or membranolide G (compound 8), or membranolide (H) (compound 9), or a composition comprising one or more of the compounds, are delivered to a subject. The compounds or compositions may be administered in various ways including oral (e.g., ingestion), intragastric, sublingual, and parenteral (referring to intravenous, intra-arterial, intramuscular, intracutaneous, topical, transdermal, intrapulmonary, intranasal, and other appropriate parenteral routes), among others.

Administration can be continuous or at distinct intervals, as can be determined by a person of ordinary skill in the art. A pharmaceutical composition can contain the active pharmaceutical ingredient and may additionally comprise a pharmaceutically acceptable vehicle or adjuvant. A pharmaceutical composition can be in the form of a solid pharmaceutical dosage form (tablet, caplet, capsule, or deliverable from an osmotic pump as examples) or syrup. *Remington's Pharmaceutical Science* provides general information regarding pharmaceutical dosage forms. (Martin, E. W., 1995, Easton Pa., Mack Publishing Company, $19^{th}$ ed.).

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one up to X carbon atoms, and includes alkyls, alkenyl, and alkynyls. For example, $C_{1-5}$ alkyl means straight or branched chain alkyl groups containing from 1 up to 5 carbon atoms. Alkoxyl means an alkyl-O— group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Cycloalkoxy means a cycloalkyl-O— group in which cycloalkyl is as defined herein. Aryl means an aromatic monocyclic or multicyclic carbocyclic ring system, including fused and spiro rings, containing from about six to about 14 carbon atoms. Aryloxy means an aryl-O— group in which the aryl group is as described herein. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described.

Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide. Arylcarbonyl means an aryl-CO— group in which the aryl group is as described herein. Heteroarylcarbonyl means a heteroaryl-CO— group in which the heteroaryl group is as described herein and heterocycloalkylcarbonyl means a heterocycloalkyl-CO— group in which the heterocycloalkyl group is as described herein. Aryloxycarbonyl means an ROC(O)— group where R is an aryl group as previously described. Heteroaryloxycarbonyl means an ROC(O)— group where R is a heteroaryl group as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, and diazaphenanthrenyl.

An "anti-leishmanial effective amount" of a compound refers to an amount effective in inhibiting proliferation or growth of a parasite in the *Leishmania* genus in the particular setting in vitro or in vivo and includes a leishmaniocidal amount against a parasite from the *Leishmania* genus.

An "anti-*Leishmania* agent" or "anti-leishmanial" agent refers to an agent that has anti-leishmanial activity in vitro and/or in vivo (inhibiting proliferation or growth of a parasite in the *Leishmania* genus in the particular setting in vitro or in vivo, including leishmaniocidal activity against a parasite from the *Leishmania* genus). The anti-*Leishmania* agent may function by any mechanism of action, such as dysregulation of the synthesis of parasite lipids which are required for membrane integrity. Examples of anti-*Leishmania* agents include, but are not limited to, antimonials (e.g., pentavalent antimonials such as sodium stibogluconate, meglumine antimonite), amphotericin B (e.g., conventional or liposomal), miltefosine (hexadecylphosphocholine), pentamidines, aminoglycoside-amino-cyclitol antibiotics (e.g., paromycin), azoles (e.g., ketoconazole, itraconazole, fluconazole), 4-methyl-6-methoxy-8-aminoquinoline (e.g., sitamaquine), and nucleoside analogues (such as a pyrazolopyrimidine, e.g., allopurinol). Other examples of anti-*Leishmania* agents include luteolin, quercetin, and isobenzofuranone compounds, such as 3,5-bis(4-chlorophenyl)-7-hydroxyisobenzofuran-1(3H)-one (JVPH3) and (2) (4-bromo)-3'-hydroxy-5'-(4-bromophenyl)-benzophenone (JVPH4), arylimidamides, such as DB766 (2,5-bis[2-(2-i-propoxy)-4-(2-pyridylimino)aminophenyl]furan hydrochloride), oxoisoaporphine alkaloids, and essential oils (e.g., essential oils of *Artemisia absinthium* L. and *Echinops kebericho Mesfin*). The anti-*Leishmania* agent may be, for example, a biologic molecule such as a polypeptide, nucleic acid, carbohydrate, or lipid, an organic small molecule (compound), a complex, an extract, etc. The anti-*Leishmania* agent may be a natural product, a derivative of a natural product, or a synthetic product. In some embodiments, the anti-*Leishmania* agent is a membranolide, such as those described herein. In other embodiments, the anti-*Leishmania* agent is not a membranolide described herein.

In vitro and in vivo methods for testing for anti-leishmanial activity can be used to evaluate candidate compounds of formula (I) and other agents of various types, including the methods described herein and elsewhere (see, for example, Tariky Y et al., *Chem Biodivers.*, 2011 April; 8(4):614-23; Bero J et al., *J Ethnopharmacol.*, 2011 Sep. 2; 137(2):998-1002; Tasdemir D et al., *Antimicrob. Agents Chemother.*, April 2006 vol. 50 no. 4 1352-1364; Rocha M N et al., *Bioinorganic Chemistry and Applications*, 2013, Volume 2013, 7 pages; Bilbao-Ramos P et al., *J Microbiol Methods*, 2012, 89: 8-11; Sobarzo-Sanchez E et al., *PLoS One* 2013 Oct. 29; 8(10):e77560; and Hanson W L et al., *Int J Parasitol.*, 1977 December; 7(6):443-7, which are each incorporated by reference in their entirety).

A "therapeutically effective amount" means an amount of the compound that can provide a therapeutic benefit to a patient against leishmaniasis.

As used herein, the term "effective amount" refers to, in some embodiments, an amount of an agent, for example, a therapeutic agent sufficient to result in the amelioration of one or more symptoms of a disorder, such as leishmaniasis. In other embodiments, a therapeutically effective amount refers to an amount of therapy, for example, a therapeutic agent sufficient to prevent advancement of a disorder. In other embodiments, a therapeutically effective amount refers to an amount of therapy, for example, a therapeutic agent sufficient to cause regression of a disorder. In other embodiments, a therapeutically effective amount refers to an amount of a therapy, for example, a therapeutic agent sufficient to enhance or improve the therapeutic effect(s) of another therapy. In some embodiments, the term "effective amount" refers to a dosage sufficient to provide treatment for a leishmaniasis infection in a subject or to kill a *Leishmania* parasite in vitro or in vivo when applied to (contacted with) the *Leishmania* parasite or its situs in vitro or in vivo. The exact amount that is required can vary, for example, depending on the target parasite, the treatment being affected, age and general condition of the subject, the particular formulation being used, the mode of administration, and the like. As such, the effective amount will vary based on the particular circumstances, and an appropriate effective amount can be determined in a particular case by one of ordinary skill in the art using only routine experimentation.

As used herein, the term "inhibiting," and grammatical equivalents, refers a reduction in biological activity or growth (e.g., proliferation). A reduction in the biological activity can include an decrease of 5%, 10%, 15%, 25%, 35%, 45%, 55%, 65%, 75%, 85%, or 95% or more, or 1.5-fold, 2-fold, 5-fold, 10-fold, 25-fold, 50-fold, 100-fold or more, of a measured biological activity in the presence of an agent(s) relative to its absence. Compounds and compositions of the invention can be used to inhibit the growth of *Leishmania* parasites and induce *Leishmania* death.

Inhibitory concentration is typically evaluated at the 50% inhibitory concentration ($IC_{50}$) Inhibition of proliferation may be attained at a lower concentration in practice, but an $IC_{50}$ concentration may be desirable.

A "prodrug" refers to a derivative of the inventive compounds that undergoes biotransformation, such as by metabolism, before exhibiting a pharmacological effect. The prodrug is formulated with the objective of improved chemical stability, improved patient acceptance and compliance, improved bioavailability, prolonged duration of action, improved organ selectivity, improved formulation (for example, increased hydrosolubility), and/or decreased side effects (for example, toxicity). The prodrug can be readily prepared from the compounds using methods known in the art, such as those described by Burger's Medicinal Chemistry and Drug Chemistry, Fifth Ed., Vol. 1, pp. 172-178, 949-982 (1995).

As used herein, the terms "treat," "treating," or "treatment" with respect to disease, in some embodiments, refers to preventing the disease (e.g., leishmaniasis), for example, causing the clinical symptoms of the disease not to develop in an animal that is exposed to or predisposed to the disease, but does not yet experience or display symptoms of the disease. In some embodiments, the term refers to inhibiting the disease, for example, arresting the development of the disease or its clinical symptoms, or delaying the onset of the disease. In some embodiments, the term refers to relieving the disease, completely or partially, for example, causing regression of the disease or its clinical symptoms.

The terms "treat," "treating," and "treatment" also refer to conferring protection against infection; preventing infection; alleviating infection; reducing the severity of symptoms and/or sequelae of infection; eliminating infection; and/or preventing relapse of infection. As used herein, the terms "treat," "treating," and "treatment" also refer to conferring protection against, preventing, alleviating, reducing the severity of, eliminating, and/or preventing relapse associated with a disease or one or more symptoms caused by a parasitic infection.

Some people have a silent cutaneous leishmaniasis infection, without any symptoms or signs. People who develop clinical evidence of infection have one or more sores on their skin. The sores can change in size and appearance over time. The sores may start out as papules (bumps) or nodules (lumps) and may end up as ulcers (like a volcano, with a raised edge and central crater); skin ulcers may be covered by scab or crust. The sores usually are painless but can be painful. Some people have swollen glands near the sores (for example, under the arm, if the sores are on the arm or hand).

Some people have a silent visceral leishmaniasis infection, without any symptoms or signs. People who develop clinical evidence of infection usually have fever, weight loss, enlargement (swelling) of the spleen and liver, and abnormal blood tests. People may have low blood counts, including a low red blood cell count (anemia), a low white blood cell count (leukopenia), and a low platelet count (thrombocytopenia).

As used herein, the terms "host", "patient", and "subject" are used interchangeably and refer to a human or non-human animal capable of being infected by a *Leishmania* parasite.

The animal can be a vertebrate. The vertebrate can be warm-blooded. The warm-blooded vertebrate can be a mammal. The mammal can be a human. The human can be an adult or a child. As used herein, the terms "host" and "subject" include human and animal hosts and subjects. Thus, veterinary therapeutic uses are provided in accordance with the method of treatment and in vitro and in vivo *Leishmania* spp. control method of the invention. As such, the presently-disclosed subject matter provides for the treatment of mammals and control of *Leishmania* in vivo in hosts such as humans, as well as those mammals of importance due to being endangered; of economic importance, such as animals raised on farms for consumption by humans; and/or animals of social importance to humans, such as animals kept as pets or in zoos. At least 70 animal species, including humans, have been found as natural reservoir hosts of *Leishmania* parasites. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The term "isolated", as used herein with respect to compounds, such as the membranolides disclosed herein, refers to compounds that are isolated from cellular components, cell culture media, or chemical or synthetic precursors.

The compounds shown in FIG. 1 are referred to interchangeably herein by their name or compound number (i.e., Aplysulphurin=compound 1; tetrahydroaplysuphurin=compound 2; membranolide A=compound 3; membranolide B=compound 4; membranolide E=compound 5; membranolide C=compound 6; membranolide D=compound 7; membranolide G=compound 8; membranolde H=compound 9; and membranolide F=compound 10).

Unless defined otherwise, technical and scientific terms used herein have the same meaning as commonly understood by one of ordinary skill in the art to which this invention belongs. Singleton et al., Dictionary of Microbiology and Molecular Biology 3$^{rd}$ ed., J. Wiley & Sons (New York, N.Y. 2001); March, Advanced Organic Chemistry Reactions, Mechanisms and Structure 5$^{th}$ ed., J. Wiley & Sons (New York, N.Y. 2001); and Sambrook and Russell, Molecular Cloning: A laboratory Manual 3.sup.rd ed., Cold Spring Harbor Laboratory Press (Cold Spring Harbor, N.Y. 2001), provide one skilled in the art with a general guide to many terms used in the present application.

EXEMPLIFIED EMBODIMENTS

Examples of embodiments of the invention include, but are not limited to:

Embodiment 1

A composition comprising an anti-*Leishmania* agent; and a compound having the following chemical structure:

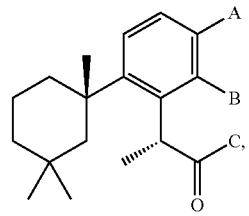

(I)

wherein A-B—C is:

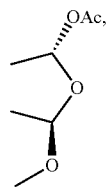

or
A-B is:

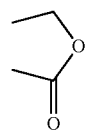

and C is:

—OMe, or
A-B is

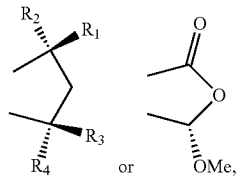

and C is:

—O$_2$H, or
A is:

and B—C is:

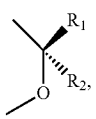

wherein R is H or alkyl, wherein $R_1$ is H and $R_2$ is alkoxyl, or $R_2$ is H and $R_1$ is alkoxyl, and
wherein $R_3$ is H and $R_4$ is alkoxyl, or $R_4$ is H and $R_3$ is alkoxyl;
or a pharmaceutically acceptable salt thereof.

2

The composition of embodiment 2, wherein R is H or $C_1$ to $C_5$ alkyl, wherein $R_1$ is H and $R_2$ is $C_1$ to $C_5$ alkoxyl, or $R_2$ is H and $R_1$ is $C_1$ to $C_5$ alkoxyl, and wherein $R_3$ is H and $R_4$ is $C_1$ to $C_5$ alkoxyl, or $R_4$ is H and $R_3$ is $C_1$ to $C_5$ alkoxyl.

3

The composition of embodiment 1 or 2, wherein the compound has a structure shown in FIG. 1, or a pharmaceutically acceptable salt thereof.

4

The composition of embodiment 1 or 2, wherein the compound does not have the structure of a compound shown in FIG. 1 or a pharmaceutically acceptable thereof.

5

The composition of any one of embodiments 1 to 4, wherein the anti-*Leishmania* agent is an antimonial, amphotericin B, miltefosine, pentamidine, aminoglycoside-aminocyclitol antibiotic, azole, 4-methyl-6-methoxy-8-aminoquinoline, or nucleoside analogue, or a combination of two or more of the foregoing.

6

A method for treatment of leishmaniasis, comprising administering an effective amount of a compound having the following structure to a subject:

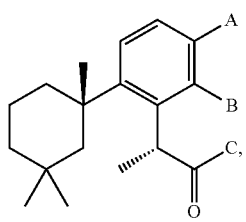

(I)

wherein A-B—C is

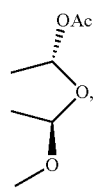

or
A-B is:

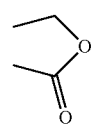

and C is:

or

A-B is

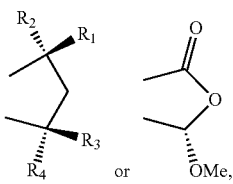

and C is:

or
A is:

and B—C is:

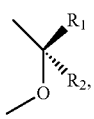

wherein R is H or alkyl, wherein $R_1$ is H and $R_2$ is alkoxyl, or $R_2$ is H and $R_1$ is alkoxyl, and
wherein $R_3$ is H and $R_4$ is alkoxyl, or $R_4$ is H and $R_3$ is alkoxyl;
or a pharmaceutically acceptable salt thereof.

7

The method of embodiment 6, wherein R is H or $C_1$ to $C_5$ alkyl, wherein $R_1$ is H and $R_2$ is $C_1$ to $C_5$ alkoxyl, or $R_2$ is H and $R_1$ is $C_1$ to $C_5$ alkoxyl, and wherein $R_3$ is H and $R_4$ is $C_1$ to $C_5$ alkoxyl, or $R_4$ is H and $R_3$ is $C_1$ to $C_5$ alkoxyl.

8

The method of embodiment 6 or 7, wherein the compound has a structure shown in FIG. 1, or a pharmaceutically acceptable salt thereof.

9

The method of embodiment 6 or 7, wherein the compound does not have the structure of a compound shown in FIG. 1 or a pharmaceutically acceptable thereof.

10

The method of any one of embodiments 6 to 9, wherein the subject is human.

11

The method of any one of embodiments 6 to 9, wherein the subject is a non-human animal.

12

The method of any one of embodiments 6 to 11, wherein the leishmaniasis is cutaneous, mucocutaneous leishmaniasis, or both.

13

The method of any one of embodiments 6 to 11, wherein the leishmaniasis is visceral leishmaniasis.

14

The method of any one of embodiments 6 to 9, wherein the leishmaniasis is caused by *L. aethiopica, L. amazonensis, L. arabica, L. braziliensis, L. dovani, L. enrietti, L. gerbilli, L. hertigi, L. infantum, L. killicki, L. major, L. martiniquensis, L. mexicana, L. peruviana, L. siamensis, L. tropica*, or *L. turanica*.

15

The method of any one of embodiments 6 to 14, wherein the subject has leishmaniasis, and the compound is administered as a therapy.

16

The method of any one of embodiments 6 to 14, wherein the subject does not have leishmaniasis, and the compound is administered as a prophylaxis.

17

The method of any one of embodiments 6 to 16, wherein the method further comprises administering an anti-*Leishmania* agent to the subject, and wherein the agent is in the same composition or a separate composition as the compound.

18

The method of embodiment 17, wherein the agent is one or more compounds having the chemical structure (I), or a pharmaceutically acceptable salt thereof (i.e., two or more compounds having the chemical structure (I), or a pharmaceutically acceptable salt thereof, are administered to the subject, within the same composition or a separate composition).

19

The method of embodiment 17, wherein the agent is not a compound having the chemical structure (I), or a pharmaceutically acceptable salt thereof.

20

The method of embodiment 17, wherein the agent is a polypeptide, nucleic acid, lipid, carbohydrate, or small molecule.

21

The method of embodiment 17, wherein the anti-*Leishmania* agent is an antimonial, amphotericin B, miltefosine, pentamidine, aminoglycoside-amino-cyclitol antibiotic, azole, 4-methyl-6-methoxy-8-aminoquinoline, or nucleoside analogue, or a combination of two or more of the foregoing.

22

The method of any one of embodiments 6 to 21, wherein the compound is administered to the subject orally or intravenously.

23

A method for controlling *Leishmania* spp. parasites, comprising applying an effective amount of a compound having the following structure to a *Leishmania* parasite, or to the situs of a *Leishmania* parasite, in vitro or in vivo:

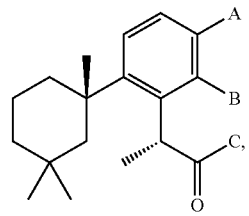
(I)

wherein A-B—C is:

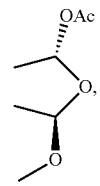

or
A-B is:

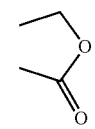

and C is:

or
A-B is

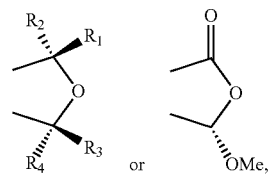

and C is:

or
A is:

and B—C is:

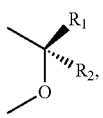

wherein R is H or alkyl, wherein $R_1$ is H and $R_2$ is alkoxyl, or $R_2$ is H and $R_1$ is alkoxyl, and
wherein $R_3$ is H and $R_4$ is alkoxyl, or $R_4$ is H and $R_3$ is alkoxyl;
or a pharmaceutically acceptable salt thereof.

24

The method of embodiment 23, wherein the compound has a structure shown in FIG. 1, or a pharmaceutically acceptable salt thereof.

25

The method of embodiment 23, wherein the compound does not have the structure of a compound shown in FIG. 1 or a pharmaceutically acceptable thereof.

26

The method of any one of embodiments 23 to 25, wherein the method further comprises applying an anti-*Leishmania* agent to the *Leishmania* parasite, or to the situs of a *Leishmania* parasite, in vitro or in vivo.

27

The method of embodiment 26, wherein the agent is one or more compounds having the chemical structure (I), or a pharmaceutically acceptable salt thereof.

28

The method of embodiment 26, wherein the agent is not a compound having the chemical structure (I), or a pharmaceutically acceptable salt thereof.

29

The method of embodiment 26, wherein the agent is a polypeptide, nucleic acid, lipid, carbohydrate, or small molecule.

30

The method of embodiment 26, wherein the anti-*Leishmania* agent is an antimonial, amphotericin B, miltefosine, pentamidine, aminoglycoside-amino-cyclitol antibiotic, azole, 4-methyl-6-methoxy-8-aminoquinoline, or nucleoside analogue, or a combination of two or more of the foregoing.

31

The method of any one of embodiments 23 to 30, wherein the *Leishmania* parasite is *L. aethiopica, L. amazonensis, L. arabica, L. braziliensis, L. dovani, L. enrietti, L. gerbilli, L. hertigi, L. infantum, L. killicki, L. major, L. martiniquensis, L. mexicana, L. peruviana, L. siamensis, L. tropica*, or *L. turanica*.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Evidence of Artifact Formation

Figure 2:
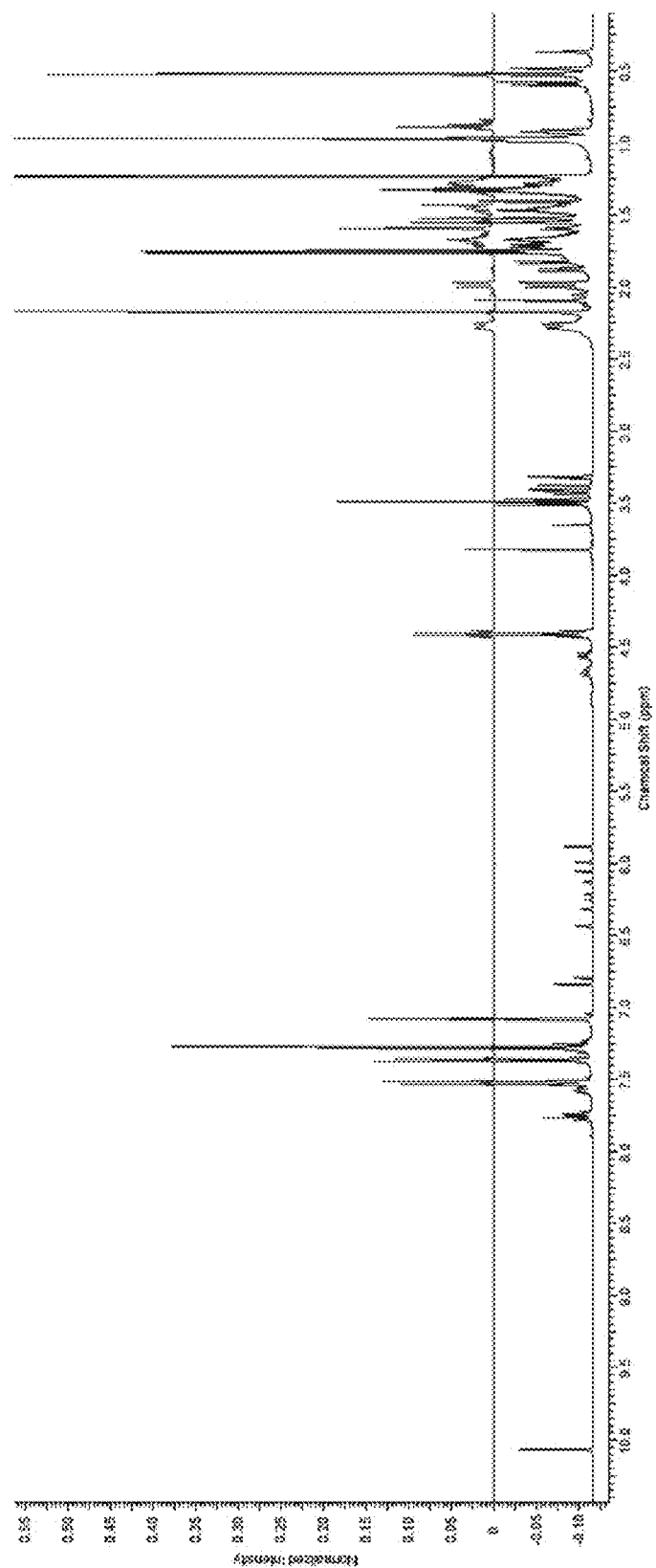
FIG. 2 shows proton nuclear magnetic resonance (NMR) spectra of aplysulphurin (red). After methanol treatment (blue), methoxy incorporation are confirmed by singlets from 3.3-3.8 ppm and acetal signals from 5.9-6.4 ppm.

Crude *D. membranosa* dichloromethane extracts were treated with methanol and monitored by LC-MS. After 12 hours, aplysulphurin peak area had decreased and new peaks with similar spectral characteristics of the methoxy membranolides appeared. Aplysulphurin was dissolved in methanol and the resulting NMR spectra (FIG. 2) confirmed the inventors' assumption.

Example 2—Compound Isolation

Aplysulphurin (24 mg) was dissolved in methanol for 24 hours and the resulting material was purified with reverse-phase (C18) HPLC. The isolated compounds were compared to their previously reported $^1$H, NOESY, and mass spectra. FIG. 3 shows an HPLC chromatogram displaying UV peaks at 254 nm (black) and 280 nm (pink) of the isolated compounds: membranolides E (5), C (6), H (9), F (10), B (4), and starting material, aplysulphurin (1).

FIG. 4 shows the proposed mechanism for the formation of the methoxy analogues from aplysulphurin.

After degradation, recovery of aplysulphurin was 60%, membranolide B was the major product isolated in a 21% yield, all other compounds were purified with <5% yield.

Example 3—Structure-Activity Study for Anti-Leishmanial Efficacy

Bioassay results for the selected compounds are shown in Table 1. Leishmaniasis efficacy was tested against *L. donovani* axenic amastigotes (amphotericin B, positive control=0.38 μM). Cytotoxicity was verified against Vero cells. Further screening utilizing the semisynthetic sample set found the two cis-di(methoxyacetal) derivatives, which have been named membranolides G (8) and H (9), with potent activity against *L. donovani* and lacking significant cytotoxicity.

TABLE 1

| Compound | Bioassay Results | |
|---|---|---|
| | IC$_{50}$ Values (μM) | |
| | Leishmania donovani | Vero Cell |
| Aplysulphurin | 1.56 | 47.7 |
| Tetrahydroaplysulphurin | 17.3 | 53.3 |
| Membranolide A | Inactive | >58.1 |
| Membranolide B | 58.1 | 44.3 |
| Membranolide C | >53.1 | 40.7 |
| Membranolide D | >53.1 | 40.7 |
| Membranolide F | 26.7 | 42.4 |
| Membranolide G | 0.82 | >53.1 |
| Membranolide H | 1.14 | >53.1 |

Some methoxy derivatives displayed greater potency against *L. donovani* than the natural products. The positioning of the methoxy groups on the furan ring appears to be important for increasing activity. Aplysulphurin, and membranolides G and H have potent activity against *L. donovani* (1.56, 0.82, and 1.14 μM, respectively) with a high selectivity index (cytotoxicity/activity).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A composition comprising at least one anti-*Leishmania* agent; and at least one other compound having the following chemical structure:

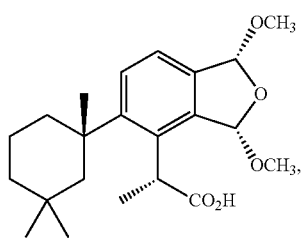 [SMILES: CO[C@@H]1O[C@H](OC)c2c1ccc([C@@]1(C)CCCC(C)(C)C1)c2[C@@H](C)C(=O)O]

or a pharmaceutically acceptable salt thereof; or,

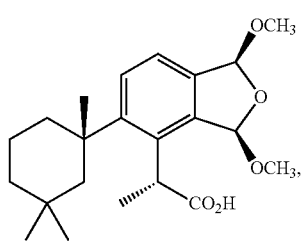 [SMILES: CO[C@H]1O[C@@H](OC)c2c1ccc([C@@]1(C)CCCC(C)(C)C1)c2[C@@H](C)C(=O)O]

or a pharmaceutically acceptable salt thereof.

2. The composition of claim 1, wherein the at least one anti-*Leishmania* agent is an antimonial, amphotericin B, miltefosine, pentamidine, aminoglycoside-amino-cyclitol antibiotic, azole, 4-methyl-6-methoxy-8-aminoquinoline, or nucleoside analogue, or a combination thereof.

3. The composition of claim 1, wherein the at least one other compound has the following chemical structure:

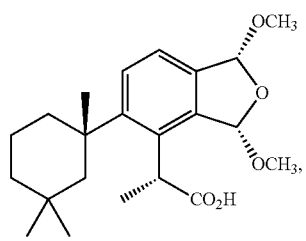 [SMILES: CO[C@@H]1O[C@H](OC)c2c1ccc([C@@]1(C)CCCC(C)(C)C1)c2[C@@H](C)C(=O)O]

or a pharmaceutically acceptable salt thereof.

4. The composition of claim 3, wherein the at least one anti-*Leishmania* agent is an antimonial, amphotericin B, miltefosine, pentamidine, aminoglycoside-amino-cyclitol antibiotic, azole, 4-methyl-6-methoxy-8-aminoquinoline, or nucleoside analogue, or a combination thereof.

5. The composition of claim 1, wherein the at least one other compound has the following chemical structure:

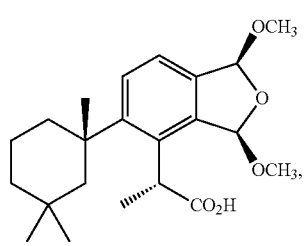 [SMILES: CO[C@H]1O[C@@H](OC)c2c1ccc([C@@]1(C)CCCC(C)(C)C1)c2[C@@H](C)C(=O)O]

or a pharmaceutically acceptable salt thereof.

6. The composition of claim 5, wherein the at least one anti-*Leishmania* agent is an antimonial, amphotericin B, miltefosine, pentamidine, aminoglycoside-amino-cyclitol antibiotic, azole, 4-methyl-6-methoxy-8-aminoquinoline, or nucleoside analogue, or a combination thereof.

7. The composition of claim 1, wherein the at least one other compound comprises a compound having the chemical structure:

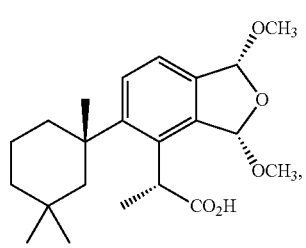 [SMILES: CO[C@@H]1O[C@H](OC)c2c1ccc([C@@]1(C)CCCC(C)(C)C1)c2[C@@H](C)C(=O)O]

or a pharmaceutically acceptable salt thereof; and a compound having the chemical structure:

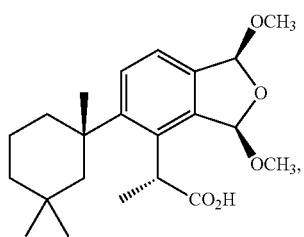 [SMILES: CO[C@H]1O[C@@H](OC)c2c1ccc([C@@]1(C)CCCC(C)(C)C1)c2[C@@H](C)C(=O)O] 5
or a pharmaceutically acceptable salt thereof.
8. The composition of claim 7, wherein the at least one anti-*Leishmania* agent is an antimonial, amphotericin B, miltefosine, pentamidine, aminoglycoside-amino-cyclitol antibiotic, azole, 4-methyl-6-methoxy-8-aminoquinoline, or nucleoside analogue, or a combination thereof.
* * * * *

UNITED STATES PATENT AND TRADEMARK OFFICE
CERTIFICATE OF CORRECTION

PATENT NO. : 9,872,849 B2
APPLICATION NO. : 14/811341
DATED : January 23, 2018
INVENTOR(S) : Baker et al.

Page 1 of 1

It is certified that error appears in the above-identified patent and that said Letters Patent is hereby corrected as shown below:

Column 30,

Lines 37-41, " 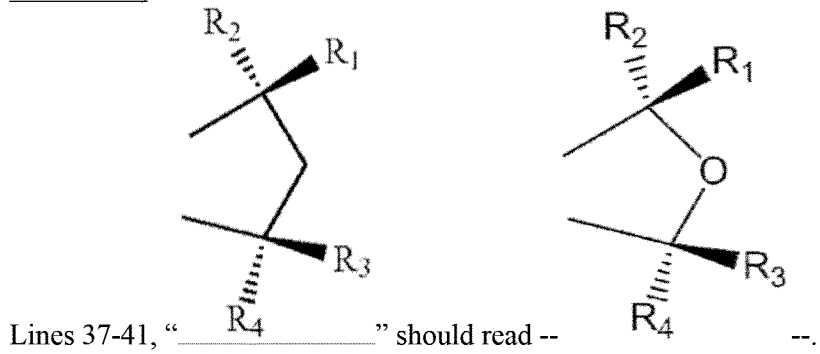 " should read -- --.

Column 32,

Lines 2-6, " 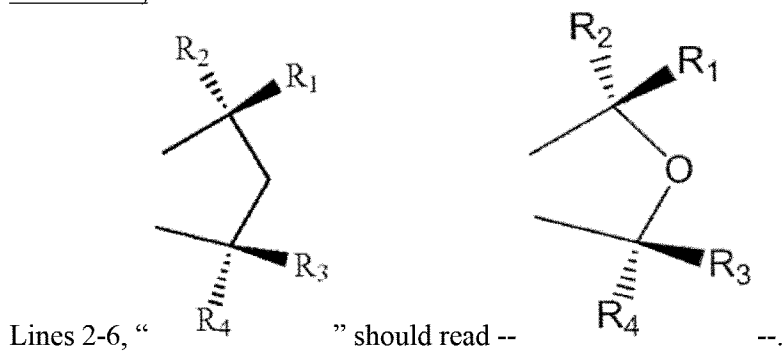 " should read -- --.

Signed and Sealed this
Second Day of October, 2018

Andrei Iancu
*Director of the United States Patent and Trademark Office*